(12) United States Patent
Anderson et al.

(10) Patent No.: US 7,531,134 B1
(45) Date of Patent: *May 12, 2009

(54) METHOD AND APPARATUS FOR AUTOMATED ANALYSIS AND CHARACTERIZATION OF CHEMICAL CONSTITUENTS OF PROCESS SOLUTIONS

(75) Inventors: Marc R. Anderson, Santa Clara, CA (US); Michael J. West, Sunnyvale, CA (US); Howard M. Kingston, Pittsburgh, PA (US); Larry N. Stewart, San Jose, CA (US)

(73) Assignee: Metara, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/094,394

(22) Filed: Mar. 8, 2002

(51) Int. Cl.
- *G01N 33/20* (2006.01)
- *G01N 33/44* (2006.01)
- *G01N 30/72* (2006.01)
- *B01D 59/44* (2006.01)
- *H01J 49/26* (2006.01)

(52) U.S. Cl. .................. 422/62; 250/281; 250/282; 422/68.1; 422/81; 436/43; 436/52; 436/53; 436/56; 436/73; 436/79; 436/80; 436/81; 436/82; 436/83; 436/84; 436/85; 436/173; 436/174; 436/179; 436/182

(58) Field of Classification Search .................. 436/43, 436/50, 52–53, 56, 73, 79–85, 173–174, 436/179, 182; 422/62, 68.1, 81; 250/281–282, 250/287

See application file for complete search history.

(56) References Cited

U.S. PATENT DOCUMENTS 4,036,590 A * 7/1977 Helder et al. .................. 436/43

(Continued)

FOREIGN PATENT DOCUMENTS

GB 2294761 * 5/1996

(Continued)

OTHER PUBLICATIONS

Marchante-Gayon, J. M. et al, Special Publication—Royal Society of Chemistry 1997, 202, 85-94.*

(Continued)

*Primary Examiner*—Arlen Soderquist
(74) *Attorney, Agent, or Firm*—Haynes & Boone, LLP.

(57) ABSTRACT

A method of directed automated analysis of a plurality of analytes of a process solution includes providing a sample of the process solution containing a plurality of the analytes, admixing an enriched isotope spike for each of the plurality of analytes to be analyzed with the process solution sample thereby effecting admixture of the enriched ratio of isotopes with the naturally occurring ratio of each analyte to be analyzed, creating ions from the spikes, introducing the ions into a mass spectrometer for determination of the identity and quantity of each analyte and delivering the information to a microprocessor. If desired, the process solution sample may be diluted and/or subjected to the addition of reagents or standards prior to initiation of the analysis. The ions may be created by an atmospheric pressure ionization interface. The information obtained is processed in a computer which serves to control other portions of the practice of the method. Such controls may include delivery of analytes to the process solution based on the information obtained, control of the sample extraction, sample handling, ionizer, and mass spectrometer. The information may also be employed to control delivery of analytes in the process solution. In another embodiment, enriched isotopic ions are introduced into the process solution. Corresponding apparatus is provided.

5 Claims, 17 Drawing Sheets

U.S. PATENT DOCUMENTS

| | | | | |
|---|---|---|---|---|
| 4,132,605 | A | | 1/1979 | Tench et al. |
| 4,324,621 | A | | 4/1982 | Kerby |
| 4,326,940 | A | * | 4/1982 | Eckles et al. ............... 204/232 |
| 4,479,852 | A | | 10/1984 | Bindra et al. |
| 4,788,700 | A | * | 11/1988 | Kurozumi et al. ............. 378/44 |
| 4,917,777 | A | | 4/1990 | Fisher |
| 5,012,052 | A | | 4/1991 | Hayes |
| 5,182,131 | A | | 1/1993 | Hashimoto et al. |
| 5,192,403 | A | | 3/1993 | Chang et al. |
| 5,287,168 | A | * | 2/1994 | Poucher et al. ............. 356/436 |
| 5,414,259 | A | | 5/1995 | Kingston |
| 5,572,024 | A | | 11/1996 | Gray et al. |
| 5,696,378 | A | | 12/1997 | Busch et al. |
| 5,703,360 | A | | 12/1997 | Fisher et al. |
| 5,777,214 | A | * | 7/1998 | Thompson et al. ......... 73/61.59 |
| 5,872,357 | A | | 2/1999 | Flanagan |
| 5,892,458 | A | * | 4/1999 | Anderer et al. ........... 340/10.41 |
| 5,983,734 | A | * | 11/1999 | Mathur et al. ............ 73/864.24 |
| 6,032,513 | A | | 3/2000 | Chorush et al. |
| 6,113,769 | A | * | 9/2000 | Uzoh et al. ................. 205/101 |
| 6,280,602 | B1 | | 8/2001 | Robertson |
| 6,726,824 | B1 | * | 4/2004 | Khosla ........................ 205/82 |

FOREIGN PATENT DOCUMENTS

| | | | |
|---|---|---|---|
| JP | 61-13153 | * | 1/1986 |
| JP | 131310 | * | 5/2000 |
| JP | 2001-296305 | * | 10/2001 |
| WO | 99/39198 | * | 8/1999 |

OTHER PUBLICATIONS

Weiderin, D. R. et al, Analytical Chemistyr 1991, 63, 1626-1631.*
Seubert, A. Fresenius J. Anal. Chem. 1999. 364, 404-409.*
Dahmen, J. et al, Fresenius J. Anal. Chem. 1997, 359, 410-413.*
Beauchemin, D. et al, Analytical Chemistry 1997, 69, 3183-3187.*
Bartels, H. et al, GIT Fachz. Lab. 1977, 21, 1276-1278 and 1280-1282.*
Slobodnik J. et al, Journal of Chromatography A 1996, 730, 353-371.*
Huang, C.-C. et al, Analytical Chemistry 1997, 69, 3930-3939.*
Multala, R. et al, Kemia-Kemi 1977, 4, 627-631.*
Parent, M. et al, Analytica Chimica Acta 1996, 320, 1-10.*
Brown, F. B. et al, Chemical Abstracts 1996, 125 abstract 315481.*
Chassaigne, H. et al, Fresenius' Journal of Analytical Chemistry 1998, 361, 267-273.*
Olesik, J. W. et al, Spectrochimica Acta, Part B 1998, 53, 239-251.*
Chastagner, P. Report 1982, DP-MS-82-76, 31 pages.*
Lee, E. D. et al, Journal of the American Chemical Society 1989, 111, 4600-4604.*
Agnes, G. R. et al, Applied Spectroscopy 1992, 46, 401-406.*
Agnes, G. R. et al, Applied Spectroscopy 1994, 48, 1347-1359.*
Facino, R. M. et al, Journal of the American Oil Chemists' Society 1995, 72, 1-9.*
Brown F. B. et al, Journal of Analytical atomic Spectrometry 1996, 11, 633-641.*
Arakawa, R. et al, International Journal of Mass Spectrometry and Ion Processes 1997, 160, 371-376.*
Brum, J. et al, Rapid Communications in Mass Spectrometry 1998, 12, 741-745.*
Pretty, J. R. et al, Rapid Communications in Mass Spectrometry 1998, 12, 1644-1652.*
Gallagher P. A. et al, Journal of Analytical atomic Spectrometry 1999, 14, 1829-1834.*
Norris, A. J. et al, Biochemistry 2001, 40, 3774-3779.*
Maxwell, S. L., III et al, Nuclear Materials Management 1990, 19, 199-202.*
Dohi, K. et al, R&D, Research and Development (Kobe Steel Ltd.) 1991, 41, 146-147.*
Agudo, M. et al, Analytica Chimica Acta 1992, 264, 265-273.*
Park, C. J. et al, Analytical Science & Technology 1995, 8, 427-434.*
Waywood, J. B., Proceedings of the Chemists' Conference 1995, 47th, 64-68.*
Ketterer, M. E. et al, Analytical Chemistry 1996, 68, 883-887.*
Jinghong, H. et al, Sensors and Actuators B 1996, 35-36, 422-426.*
Stewart, I. I. et al, Journal of Analytical Atomic Spectrometry 1996, 11, 1203-1214.*
Olesik, J. W. et al, Journal of Analytical Atomic Spectrometry 1997, 12, 507-515.*
Zoorob, G. et al, Journal of Analytical Atomic Spectrometry 1997, 12, 517-524.*
Baron, D. et al, Journal of Environmental Quality 1998, 27, 844-850.*
Raffaelli, A. et al, Inorganica Chimica Acta 1998, 275-276, 462-469.*
May, T. W. et al, Atomic Spectroscopy 1998, 19, 143-149.*
Ross, A. R. S. et al, Analytical Chemistry 1998, 70, 2225-2235.*
Schramel, O. et al, ournal of Chromatography, A 1998, 819, 231-242.*
Godec, R. et al, Semiconductor Pure Water and Chemicals Conference 1999, 18th, 91-110.*
Szpunar, J. et al, Chemia Analityczna (Warsaw) 1999, 44, 351-362.*
Henderson, W. et al, Inorganica Chimica Acta 1999, 294, 183-192.*
Mollah, S. et al, Analytical Chemistry 2000, 72, 985-991.*
Hawk, G. L. et al, International Laboratory 1982, 12, 48-56.*
Marabini, M. A. et al, Microchemical Journal 1992, 46, 302-312.*
Igarashi, H. et al, Nuclear Technology 1993, 102, 287-296.*
Beary, E. S. et al, Journal of Analytical Atomic Spectrometry 1994, 9, 1363-1369.*
Sushida, K., Journal of the Mass Spectrometry Society of Japan 1997, 45, 159-174.*
Hoelzl, R. et al, Accreditation and Quality Assurance 1998, 3, 185-188.*
Frary, B, D., Analyst 1998, 123, 233-237.*
Martin, J. M. et al, Applied Spectroscopy 1987, 41, 986-993.*
Turnlund, J. R. et al, Journal of Micronutrient Analysis 1990, 7, 117-145.*
Goossens, J. et al, Analytica Chimica Acta 1994, 293, 171-181.*
Davis, B. R. et al, AT-Process 1995, 1, 115-120.*
Oquendo, J. N. et al, Analytical Chemistry 1989, 61, 1791-1792.*
Perkins, R. et al, LC-GC 1990, 8, 238, 240-241.*
Heumann, K. G. et al, Spectrochimica Acta, Part B 1998, 53, 273-287.*
Applications of Isotope Dilution-Mass Spectrometry in Clinical Chemistry, Pharmacokinetics and Toxicology, Mass Spectrometry Reviews, pp. 249-307 (1992).
Newton, B. et al., Analysis of Copper Plating Baths—Suppressors and Levelers, Electrochemical Society Proceedings, pp. 1-5, V2000-27.
International Technology Roadmap for Semiconductors 1999 Edition: Defect Reduction, Sematech, Austin, TX, pp. 269-293.
Stewart, I.I., Electrospray mass spectrometry: a tool for elemental speciation, Spectrochimica, Acta. Part-B 54 (1999) 1649-1695.
Cole, R. B., Electrospray Ionization Mass Spectrometry: Fundamentals, Instrumentation & Applications, John Wiley & Sons, Inc., 1997, New York.
Rottmann, L. et al., Development of an on-line isotope dilution technique with HPLC/ICP-MS for the accurate determination of elemental species, Fresenius J. Anal Chem., (1994) 221-227 V350.
Rottmann, L. et al., Determination of Heavy Metal Interactions with Dissolved Organic Materials in Natural Aquatic Systems by Coupling High-Performance Liquid Chromatography System with an Inductively Coupled Plasma Mass Spectrometer, Anal. Chem., (1994) 3709-3715 V66.
Heumann, K. G. et al., Elemental Speciation with Liquid Chromatography-Inductively Coupled Plasma Isotope Dilution Mass Spectrometry, J. Anal. Atom. Spectro. (1994) 1351-1355 V9.
Horn, M. et al., Comparison of heavy metal analyses in hydrofluoric acid used in microelectonic industry by ICP-MS and thermal ionization isotope dilution mass spectrometry, Fresenius J. Anal. Chem (1994) 286-292 V350.
Viczian, Miklos et al., On-line Isotope Dilution and Sample Dilution by Flow Injection and Inductively Coupled Plasma Mass Spectrometry, J. Anal. Atom. Spectro., (1990) 125-133 V5.

Fassett, J.D., et al., Isotope Dilution Mass Spectrometry for Accurate Elemental Analysis, Anal. Chem. (1989) 643A-649A V61, No. 10.

Fassett, J.D. et al., Determination of Nanogram Quantities of Vanadium in Biological Material by Isotope Dilution Thermal Ionization Mass Spectrometry with Ion Counting Detection, Anal. Chem., (1985) 2474-2478 V57, No. 13.

* cited by examiner

METHOD AND APPARATUS FOR AUTOMATED ANALYSIS AND CHARACTERIZATION OF CHEMICAL CONSTITUENTS OF PROCESS SOLUTIONS

BACKGROUND OF THE INVENTION

1. Field of the Invention

The invention relates to a method and apparatus for rapid in-process, automated analysis resulting in characterization by direct measurement of relevant chemical constituents of a process solution. More specifically, the method preferably uses a combination of simultaneous measurements utilizing the techniques of In-Process, Isotope Dilution Threshold and Quantification Measurement Mass Spectrometry (IPMS) and Speciated Isotope Dilution Mass Spectrometry (SIDMS) to identify and quantify chemical reagents and their reaction products in a process solution. In addition, this method also uses a technique of quantitation by internal standard. The apparatus preferably consists of a sample handling instrument for Automated Analysis in Fluid based Processing (AAFP), coupled to an In-Process, Atmospheric Pressure Ionizer, Mass Spectrometer (IP-API-MS) that is configured to identify and quantify relevant chemical constituents of a liquid sample.

2. Cross Reference to Related Documents

The present application is related to (a) issued U.S. Pat. No. 5,414,259, issued to Howard M. Kingston on May 9, 1995, incorporated herein in its entirety by reference, and to (b) co-pending patent application Ser. No. 09/015,469, filed Jan. 29, 1998, also incorporated in its entirety by reference, and to (c) a co-pending patent application filed Dec. 4, 2001, bearing Ser. No. 10/004,627, which is also incorporated herein in its entirety by reference, and to (d) U.S. Ser. No. 10/086,025 filed Feb. 28, 2002, which is a non-provisional application based on co-pending provisional patent application Ser. No. 60/305,437, filed Jul. 13, 2001, also incorporated in its entirety by reference.

3. Description of the Prior Art

Characterization and maintenance of many process solutions is critical to the functioning of that solution. Information provided during characterization can enable the process engineer to assess the quality of the process and adjust the constituents to optimize the results. Frequently, knowledge of all relevant species is critical to the understanding and control of the chemical mechanisms being employed. The ability to determine all relevant species simultaneously and in real-time has been an unsatisfied goal for chemical process management. One such example is that of monitoring the concentration of additives and reagents in a metal electroplating (electrodeposition of electroless deposition) bath. The properties of a deposited metal are affected significantly by the inclusion of organic additives in the deposition solution. Historically these additives have been assigned functions such as 'accelerators', 'suppressors', 'levelers' and 'brighteners'—labels that describe their effect on the rate of the electrodeposition of the metal and its morphology. In addition the properties of the metal plate will be affected by the concentration of the metal being plated. During plating the metal in solution will be reduced unless replenished such as by use of a soluble anode or by addition of metal salts to the solution. Additional reagents perform the function of electrolytes to maintain the conductivity of the solution, acids or bases are added to balance the solution pH, and other constituents are added to enhance the effect of the organic additives. The balance of these ingredients is even more critical in the semiconductor industry where metal deposition into high-aspect ratio features must be performed without defects. As the architecture of the integrated circuit continues to shrink effective metal interconnect depositions require stringent plating conditions.

The most basic approach in maintaining proper plating conditions is to replenish those plating components which are known to be depleted during deposition according to the rate of deposition. While this method can result in a uniform rate of metal deposition, the resulting film has been shown in one study to contain increasing contamination from carbon and sulfur atoms produced during the breakdown of the organic additives. Reduction of film contaminants is frequently achieved by either of two processes, (i) "batch dumping", or (ii) "bleed and feed" in which a percentage of the plating solution is removed and replenished with fresh solution. The percentage of the solution that is removed in a "bleed and feed" process and the frequency of "batch dumping" are generally derived by experience. Both methods of solution control are wasteful and result in deposited films with a steady state level of contamination. The level of contamination in the film is still subject to change with significant fluctuations in process contamination.

In the semiconductor industry contamination is controlled by higher bleed-and-feed rates with a "remove-and-reconstitute" approach having recently been suggested. The remove-and-reconstitute step involves complete removal of all organic compounds followed by addition of fresh additives prior to recycling the base plating solution. Unfortunately, this approach provides no informative data regarding the plating process, and as unexpected results seem the norm when ECP [electrochemical plating] chemistries are tweaked—clearly, precise, real time, direct measurement of ECP chemistries are highly desired.

A number of other prior arts are used which can provide partial information about the constituents of an electroplating bath, but are susceptible to interferences, are incomplete, and are slow.

The most common approach to monitoring an electroplating or electroless plating bath is by electrochemical techniques. Electrochemical techniques use indirect methods of monitoring the concentrations of the organic additives. Direct measurement of the additive or byproduct is not possible unless they are electrochemically active within the potential range of the detector and no interferences are present. One of the earliest electrochemical techniques, referred to as Cyclic Voltammetric Stripping (CVS), involves placing an inert working, or indicator, electrode in the plating solution and applying a potential sufficient to deposit the metal onto the electrode surface. The potential is then shifted more positive to the point where the plated metal is oxidized, or stripped, off of the electrode surface. The corresponding current of the stripping wave is integrated to get the total charge, and the charge determines the quantity of the metal that was deposited. See U.S. Pat. No. 4,132,605. This deposition quantity relates indirectly to the efficiency of the plating solution, but provides very little information about the constituents of a complex plating mixture. In addition, the working electrode surface tends to become contaminated by additive byproducts and eventually sensitivity is lost with continuous use. Follow up improvements to this prior art simply extended the working life of the indicator electrode for a short time by adding a cleaning step to the process by introducing pulsed CVS techniques.

An improved technique was suggested in U.S. Pat. No. 4,917,777 in which an open circuit pause step was inserted after the cleansing step in which contaminants were removed by a mechanism not fully understood. See U.S. Pat. No. 4,917,777. These pulsed CVS improvements extended the active life of the indicator electrodes; however, exact information regarding the characterization of additives and degradation byproducts remained unknown.

A number of other prior art disclosures attempt to relate the concentration of additives to the kinetic behavior of the deposition process. In U.S. Pat. No. 4,324,621 an attempt to characterize organic additives was made by measuring the overpotential between reference and indicator electrodes at the point at which deposition begins. The overpotential required for deposition is affected by the organic additives, electrolytes, and impurities in the plating solution. By measuring this potential difference between the overpotential and the reversible metal reduction potential with varying concentrations of organic additives and correlating these with the physical condition of the film an indirect method of characterizing the plating solution was said to be established. A version of this technique is presented in U.S. Pat. No. 4,479,852 where the indicator electrode is first plated with the deposition metal and the equilibrium potential serves as the reference for the overpotential measurement. These techniques provided indirect data about the condition of a plating solution and are best used in plating solutions with no more than one additive. In solutions with multiple additives and impurities—each contributing in a different way to the plating efficiency—the foregoing techniques are incapable of providing the depth of information needed for proper bath maintenance. Evidence of this difficulty is provided in U.S. Pat. No. 5,192,403 where it is pointed out that when the ratio of two additives change the standard CVS technique is no longer applicable. The solution presented in this patent is to measure one of the two additives by a different technique (HPLC) and apply this result to the results obtained electrochemically.

In order to provide more information regarding the condition of a process bath with multiple organic additives and impurities, complex and slow calibration schemes are generally necessary. In U.S. Pat. No. 5,192,403 the usual calibration scheme is described in which a standard is added to a stock solution multiple times to generate a traditional calibration curve and then several aliquots of the unknown plating bath are added to an additional stock solution to obtain a similar curve for the unknown. This process is time consuming and can take 2 hours to provide results. Even moderately slow changes in additive or impurity will not be detected. To respond to this problem recent improvements to prior art electrochemical techniques involve accelerating the measurement speed. For example, in U.S. Pat. No. 5,182,131 the improvement suggested is a combination of determining the concentration of the consumable ingredient by a calculated method and is coupled with intermittent measuring of the consumable compound to verify the calculated values. This technique requires the surface area of the deposition surface to be known. Reliance on calculated values will work only if the rates of consumption are well established. This technique does not serve to monitor or identify by-products, or to quantify those additives that are not consumed at predictable rates.

Another method attempting to increase the reporting speed is presented in U.S. Pat. No. 6,280,602. Here the electrochemical reporting time is reduced by keeping the reference electrode exposed to the plating bath solution to be tested. This is done to shorten the equilibration time required prior to the measurement. However, each of the standard steps of preparing a basis solution, preparing a calibration solution, providing a calibration curve for each component to be measured, and comparing the slopes of both calibration curve and unknown sample curve need to be performed. While an improvement to existing techniques, the complex sample preparation and calibration still remains the limiting step in the rapidity of the measurement. An additional goal of Robertson's U.S. Pat. No. 6,280,602 was to provide an increase in the precision of existing methods to a level of preferably less than 10 percent.

Recent publications have introduced the use of chromatography to separate the individual additives before detection in order to make quantitative measurements of the additives and impurities. *Analysis of Copper Plating Baths Suppressors and Levelers*, B. Newton, et al., *Proc. Electrochem Soc.*, *V*2000-27, page 1, December, 2000. Chromatography serves to separate the additives and impurities from other species that may interfere with their detection. Problems with interferences are not eliminated, only minimized using this technology. In Newton's work it is noted that the excess of sulfuric acid and copper sulfate in solution obscures the detection of some of the additives and byproducts. The use of chromatographic methods is time-consuming and produces delays in data reporting similar to the electrochemical methods mentioned previously. The solution to be tested must be spiked with standard organic additives of known concentration both to identify each additive and to generate a calibration curve in order to quantify them. Each separation step requires an elution time of ca. 20 minutes for completion. In addition, the chromatographic technique does not provide data that make identification of unexpected by-products or contaminants possible. Identification of unknown compounds whose presence is not predicted by an understanding of the process necessitates a different method to be used to identify the compounds followed by synthesis and spiking the sample. Assessment of the decomposition of the high molecular weight polymers used in an acid plating bath cannot be achieved using the robust chromatographic materials required in Newton.

The use of isotopes as part of an innovative process necessitates the examination of other applications that monitor similar components or that use novel methods to achieve these measurements. Isotopes have been used to measure components of interest. U.S. Pat. No. 4,975,378 discloses a specific method of indirect detection in chromatography. This method uses radioactive elements made into derivatives of the analyte of interest to be detected. The non-labeled analyte of interest and the labeled radioactive analyte of interest exit the chromatographic column together and the radioactive signature of the analyte of interest signals the arrival of the chromatographic fraction containing the analyte of interest. This is an indirect detection method. This disclosure is very specific and limited to column chromatography and indirect detection.

U.S. Pat. No. 5,696,378 demonstrates the determination of chlorine based on flame infrared emission spectrometry (ID-FIRE) using isotope dilution with detection by the infrared technique. The use of infrared was seen as an advantage as compared with sample preparation used in mass spectrometry. The mixture of chlorine and the isotopically enriched chlorine spike are mixed and excited thermally to permit infrared measurement of the isotopes. Thermal excitation could alter or destroy many of the species that are being analyzed in complex material. While this method works for isolated chlorine, it is not suited for chlorine in complex material combinations or for identification in fragile structures. This is fundamentally very different from mass spectrometric measurements where sample preparation is not a thermal process and where ionization uses very different mechanisms that are integral to the process of measurement.

In summary, prior art methods and apparatus for measuring and quantifying the chemical constituents consist mostly of indirect methods that are slow, inaccurate, and provide only some of the information needed for optimization of process solutions. Most modern process monitoring tools use various combinations of the aforementioned prior art in order to provide as much information as can be gathered. No one prior art method will do all additives in a short analysis time with good sensitivity.

SUMMARY OF THE INVENTION

In accordance with one aspect of the invention, a method of analysis of a constituent in a sample of process solution is provided. The method includes the acts of: (a) diluting the sample to provide a diluted sample; (b) mixing a spike with the diluted sample to allow equilibrium to occur therebetween; (c) ionizing the equilibrated diluted sample and spike in an atmospheric pressure ionizer (API) to produce ions; (d) processing the ions in a mass spectrometer to provide a ratio response; (e) characterizing the concentration of the constituent in the sample using the ratio response; and (f) cyclically repeating acts (a) through (e) under machine control to automatically monitor the concentration of the constituent in the process solution over time.

In accordance with another aspect of the invention, an apparatus for automated analysis of constituents of a process solution is provided. The apparatus includes: a sample extraction module operable to extract a sample from the process solution; a sample dilution module operable to dilute the sample to provide a diluted sample; a mixer for mixing the diluted sample and a spike to allow equilibration to occur therebetween; an atmospheric pressure ionizer operable to ionize the equilibrated diluted sample and spike mixture to produce ions; a mass spectrometer operable to process the ions to provide a ratio response; and a control system operable to control the cyclic extraction of samples, dilution of the samples, spiking of the diluted samples, ionization of the spiked diluted samples, processing of the ions to provide ratio responses, and processing of the ratio responses to characterize the concentration of the constituent in the process solution over time.

DESCRIPTION OF THE PREFERRED EMBODIMENTS

As employed herein, the term "process solution" shall include (a) solutions employed in an industrial manufacturing facility or laboratory and (b) environmental solutions, including but not limited to, water and (c) other solutions desired to be chemically analyzed.

As employed herein, "complex species" means molecules containing both organic and inorganic constituents.

As employed herein, the term "analyte" shall include organic compounds, inorganic compounds, elements, ions and complex species.

As employed herein, the term "impurities" shall include (a) degradation products of the organic additive decomposition, (b) contaminates and (c) by-products of additives consumed.

As employed herein, the term "remote' means at a location not immediately adjacent to the source from which the process solution sample is extracted.

As employed herein, the term "real-time" as employed in connection with a process meaning a time period which is brief and in no event greater than the duration of a cycle of the process.

Figure 1:
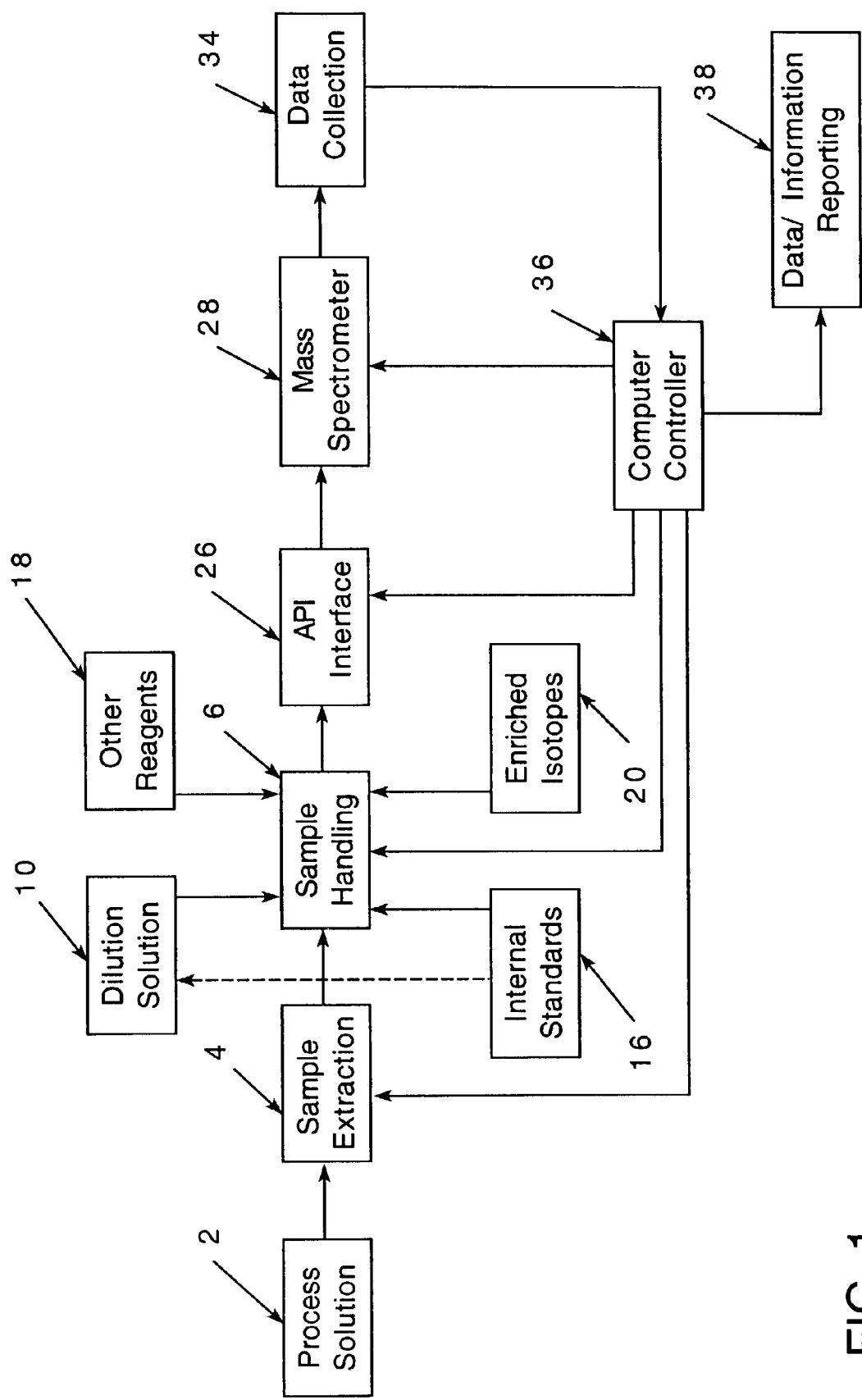
FIG. 1 is a schematic illustration showing a form of method of the present invention.

Turning to FIG. 1, there is shown a schematic of a form of method of the present invention. A process solution 2 which is the subject of the analysis being performed has a sample extracted 4. This can be accomplished on a continuous or periodic basis. It is delivered to sample handling 6 to a region which permits alteration of the sample by certain desired additions. More specifically, at the sample handling 6, if desired, the sample may be diluted 10 in order to facilitate optimal measurement and, in some instances, to reduce the cost of the procedure. This dilution solution may contain internal standards 16. Other reagents 18 such as pH adjustment or control of adducts for polymer analysis, for example, may be added. Certain internal standards 16 may be added to the sample handling station 6 and, if desired, to the dilution solution 10 to facilitate quantification. The enriched isotopes 20 which are employed in effecting the preparation of the sample for the API-MS (atmospheric ionized) spectrometer processing are added for purposes which will be described in greater detail herein. The API will generally have two conduits, one for positive ions and one for negative ions, which will be run at different time periods. The modified sample contained in the sample handling unit 6 is then introduced into the API electrospray interface 26 wherein the sample is converted into an ion beam which is introduced into mass spectrometer 28 with data collection 34 serving to ascertain the results of the quantitative and qualitative analysis of the analytes contained within the extracted sample. The output of the data collection unit 34 is delivered to the computer controller 36 which may emit information to the data/information reporting unit 38 for visual display, preparation of hard copy, or storage with or without additional processing, for example. The computer controller 36 serves to, through the indicated lines, have output determining when sample extraction 4 will occur, the interaction with sample handling unit 6 and the operation of API electrospray interface 26 and mass spectrometer 28. Certain refinements and preferred process steps will be discussed hereinafter.

The subcomponent of the apparatus may be of any suitable type such as that disclosed in U.S. Ser. No. (to be provided when received) filed Feb. 28, 2002 and based on provisional Ser. No. 60/305,437.

In a preferred embodiment of the present apparatus a sample handling and extraction module is connected to a process bath or other source of process solution by tubing by a mini-reservoir in the apparatus. The mini-reservoir provides a rapid transfer point for the process sample and isolation of the process solution itself from enriched isotope spike solutions used in the apparatus. The mini-reservoir also provides a point near the process solution where enriched isotope solutions can be added in order to resist any losses of analytes by interaction with the walls of the tubing and of the sample handling apparatus do not generate error in the quantitative analysis. Propulsion of the sample through the sample handling apparatus will be provided by multiple pumping apparatus. Multiple pumping apparatus allow one pump to be loaded with sample while the previous pump is propelling the sample to the detector.

In yet another embodiment of the apparatus the process solution to be monitored can be diluted in a known manner with an inert solvent in order to adjust the concentration to a level optimized for ionization and introduction to the detector. This enables the apparatus to optimize the instrument sensitivity for detection of lower levels of additives, impurities, and by-products.

In another aspect to the apparatus the sample to be characterized may be diluted for reasons such as reducing the concentration of the electrolytes in the sample prior to analysis. This dilution must be accomplished precisely and consistently in order to minimize error in the monitoring method. In one embodiment this is accomplished by pumping the sample to be characterized through a capturing reservoir of fixed volume that is physically identical to a sample loop as commonly used in liquid chromatography apparatus. A valve mechanism is provided that can then direct the captured sample into a pumping reservoir containing a precise volume of dilution solution. In one embodiment of the present invention the pumping reservoir is a syringe pump. In another embodiment of the invention an additional pumping reservoir is provided and operated in opposition to the first pumping reservoir to enable mixing of the sample and dilution solutions.

In an additional embodiment an isotopically enriched spike may be diluted precisely and consistently by using a capturing reservoir of fixed volume in the same manner as described in the preceding paragraph. In one embodiment multiple fixed volume reservoirs can be placed in parallel in a switching mechanism to enable variable dilutions to be made.

The subcomponent of the apparatus may be of any suitable type such as that disclosed in U.S. Ser. No. 10/086,025 filed Feb. 28, 2002 and based on provisional Ser. No. 60/305,437.

Figure 2:
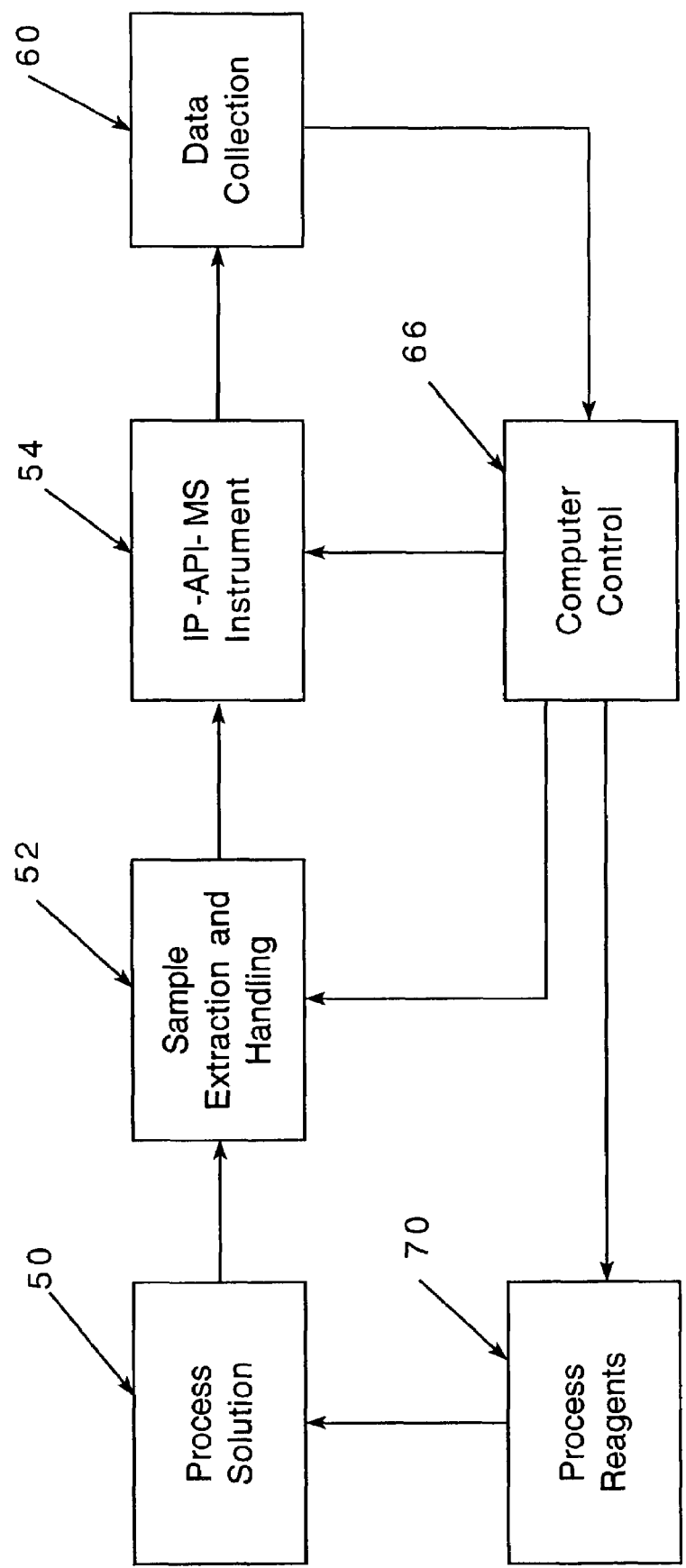
FIG. 2 is a flow chart showing a form of apparatus of the present invention employing full reagent monitoring.

Referring to FIG. 2, a block diagram of a modified form of apparatus showing feedback control is provided. In this system, the process solution 50 has a sample extracted and delivered by sample extraction and handling unit 52 which in turn delivers the same with or without additional materials to IP-API-MS instrument 54 with the output thereof containing the analytical data regarding quantity and quality of a plurality of analytes being delivered to data collection 60 which delivers information regarding the analysis to computer control 66. Computer control 66 has outputs controlling process reagents 70 which deliver materials to the process solution 50, thereby adjusting the process reagent concentrations.

Figure 3:
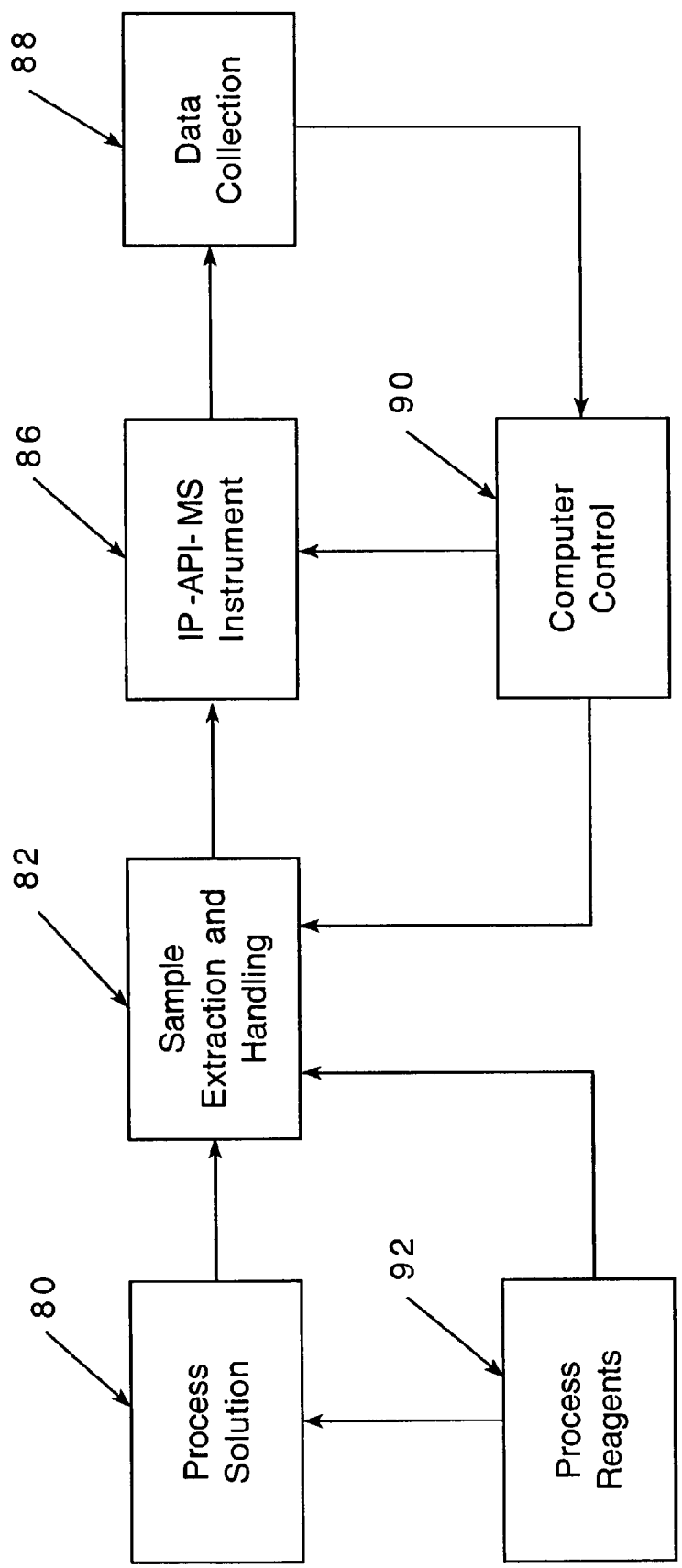
FIG. 3 is a flow chart showing a form of apparatus of the present invention having feedback control.

Referring to FIG. 3, there is shown a schematic diagram of a form of apparatus employable in the present invention to monitor process reagents. Hardware is disclosed in U.S. Ser. No. 10/086,025, filed Feb. 28, 2002 and incorporated herein by reference on page 1 of this Application, and alternate apparatus will be known to those skilled in the art. Details regarding the specific equipment selected need not be disclosed herein. The process solution 80 is contained within a suitable vessel and has apparatus for sample extraction and handling 82 which may be associated with various additional materials to be added to the sample as discussed in connection with FIG. 1. The sample is then introduced into the IP-API-MS instrument 86 with the data being received at data collection 88 and delivered to computer control 90 which, in the form shown, has an output controlling the sample extraction and handling unit 82, as well as the IP-API-MS instrument 86.

The sample extraction and handling unit 82 may be controlled by computer control 90 to draw samples from the process solution reservoir 92 in order to monitor process reagent condition.

While any suitable mass spectrometer may be employed, it is preferred to employ a high resolution mass spectrometer having a mass resolution of 1500 or greater such as a time of flight mass spectrometer, a quadrapole, an ion trap or an ICR (Ion Cyclotron Resonance).

One of the features of the present invention is the rapid, generally real-time manner in which the direct analysis may be effected. Exclusive of those situations where pretreatment might be required and any time involved in such situations, the present invention generally permits a complete, direct qualitative and quantitative analysis of a plurality of analytes to be completed in less than about 10 minutes and generally less than about 3 minutes.

Figure 4:
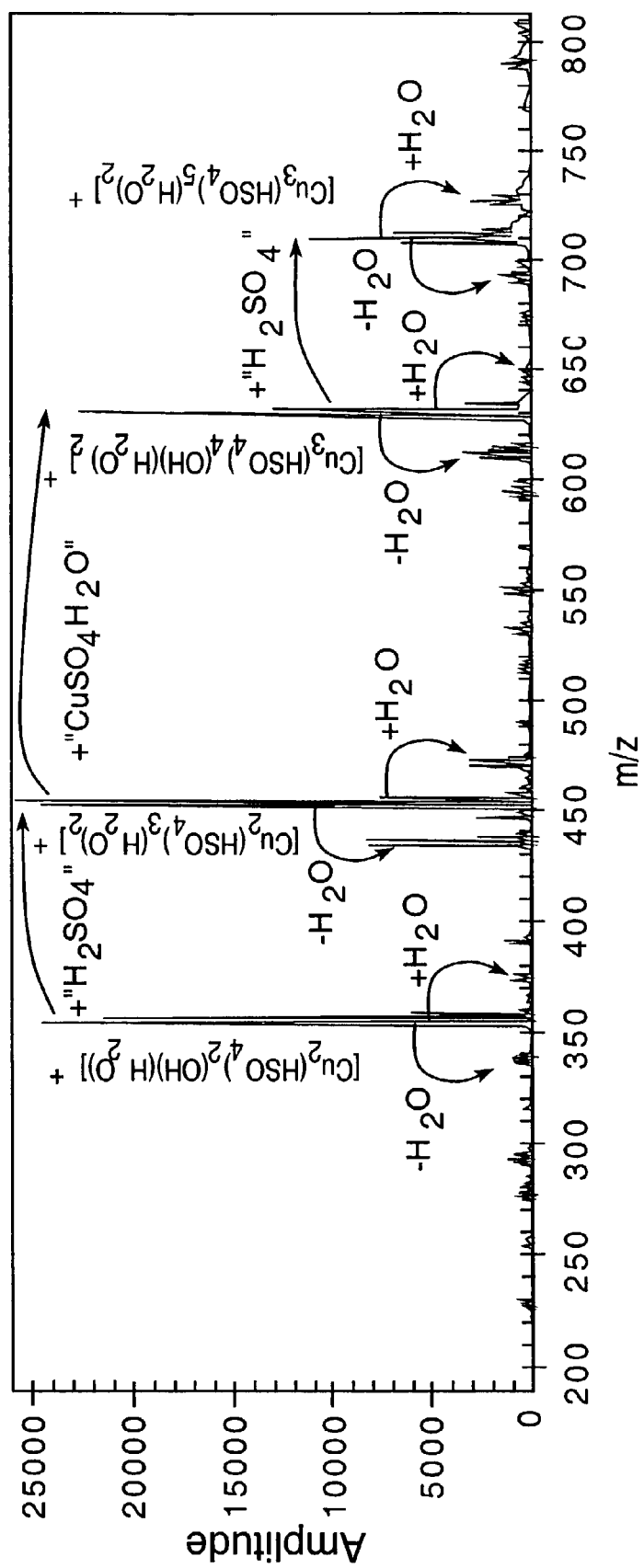
FIG. 4 shows a plot of mass to charge versus amplitude for species identification in accordance with the present invention illustrating complexes formed by copper sulfate and sulfuric acid.

This invention provides a method and apparatus for a liquid handling, in-process, atmospheric pressure ionization, mass spectrometer instrument that can use enriched stable isotopes to rapidly and precisely quantify a plurality of analytes or species in a process solution. The spiking of the enriched isotopes in species form may be accomplished by "dynamic spiking method" which supplies a known quantity of enriched isotope ions to the solution to be measured. This enriched isotope ion is then complexed by process chemical constituents in the process solution. These solution components incorporate the enriched isotope in a dynamic interaction based on stability of complexes and formation constants forming the same species that are naturally occurring in solution. An example of this embodiment of the method is demonstrated for specific molecular forms involved in plating solutions here in this example. In one embodiment the complexes of copper ion with bis(3-sulfopropyl)disulfide are formed dynamically to [Cu(O$_3$S(CH$_2$)$_3$SS (CH$_2$)$_3$SO$_3$H]$^+$ (designated Cu'SPS' species). This molecular ligand of copper is one of the reactive species known as "accelerators" and used in copper electrodeposition solutions. In this fashion it is isotopically tagged (or spiked) with enriched copper ion and is measured along with other naturally occurring copper species of interest in solution. This dynamic spiking method permits the formation of complex isotopically enriched species in solution, thus enabling quantification of the species and tracking and identification of sub-species and artifacts created in the ionization and chemical manipulation portion of the analysis. The example ligand complex, the Cu'SPS' species, is formed in solution dynamically with the enriched isotopic ion and if sub-species are formed from this isotopically labeled ion in the ionization process, chemical manipulation (transport or solution modification) of these related sub-species are distinguished in the spectrum as they are isotopically labeled. Direct applications using the techniques are also demonstrated in the formation of multiple species of copper sulfate in water after electrospray ionization. The following FIG. 4 identifies many of these species that were dynamically formed in solution by copper sulfate and sulfuric acid.

The addition of enriched isotopes is used to make the measurements relevant to true quantitative values. Normally there is a bias created in the electrospray mass spectrometers that is inversely related to the ionic content (total ionic concentration of the entire solution) of the sample. This causes a bias between different samples and the blank that must be subtracted and the sample it is supposed to represent and be subtracted from. Normally matrix matching must be applied to that blank. However, in this invention this requirement is eliminated. The use of calibration curves is normally necessary, but they are biased in these cases based on the ionic content making a single calibration curve inappropriate. In this invention by using both direct in-process isotope dilution measurements and speciated isotope dilution measurements the blank returns a true unbiased answer to permit direct subtraction from any sample matrix. The blank is unbiased as the blank is measured in any ionic strength different from that of the sample and no attempt is made to matrix match. Despite an increase (or decrease) in absolute signal intensity the isotopic ratio determines the true concentration of the element, species or molecule independent of the ionic content of the sample, blank or matrix solution. The true value is obtained without bias due to ionic yield in the electrospray ionization source.

The sample likewise has the same relative intensity dependence with ionization strength using electrospray and other techniques. By using direct in-process isotope dilution and speciated isotope dilution measurements the relative intensity of the signal no longer effects the quantification of the analytes in the sample. A direct measurement of the concentration is established by the isotopic ratio and the unbiased concentration is achieved. In this way can unknown samples of unknown ionic strength and composition be placed into the instrument without performing calibration curves and accurate concentrations enabled to be determined. These concentrations are independent of ionic strength, sample matrix composition and intensity fluctuations of the instrument.

Figure 5:
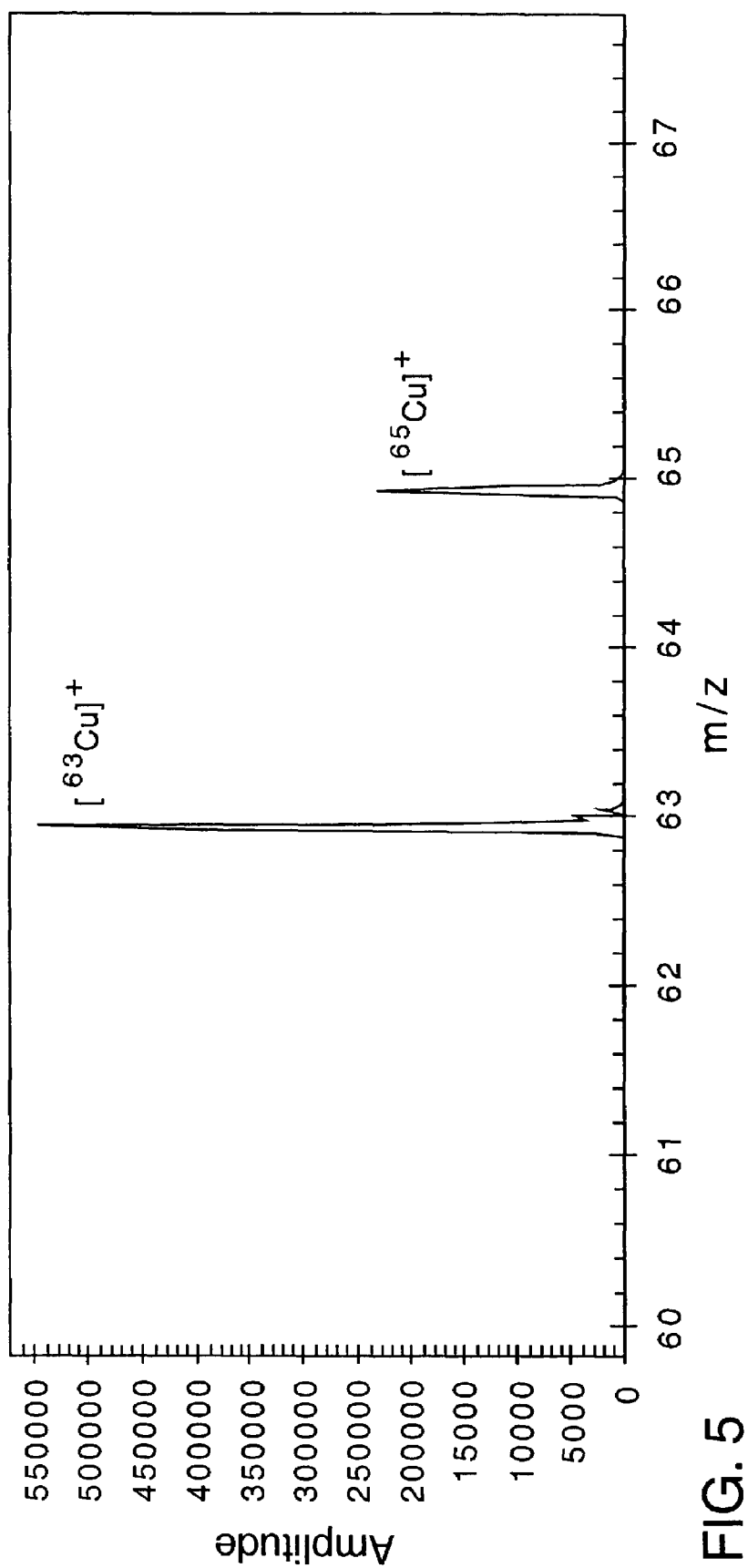
FIG. 5 illustrates the natural copper ratio observed in a dilute electroplating solution.
Figure 6:
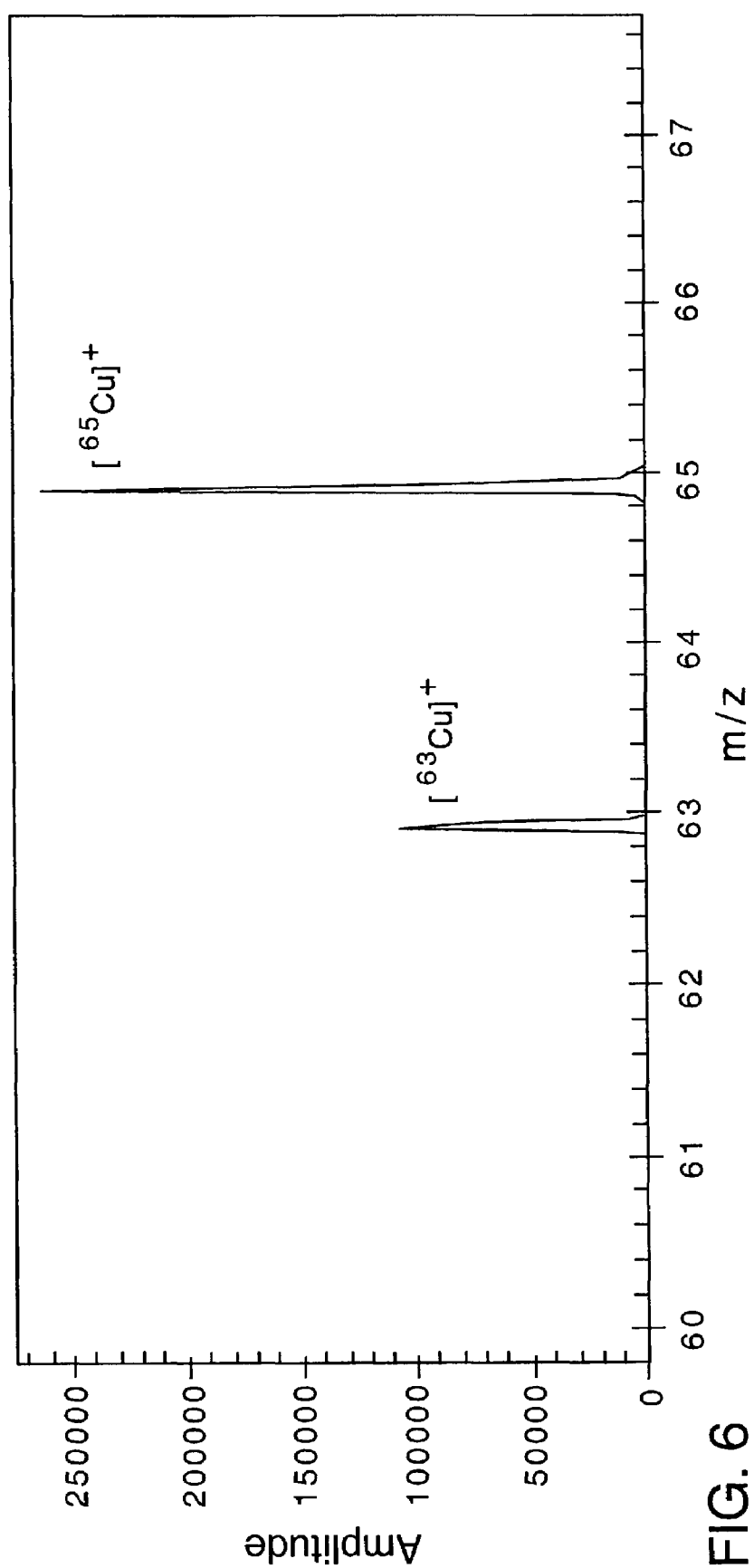
FIG. 6 illustrates the altered ratio created by mixing of a diluted plating solution of natural isotopic composition and an isotopically enriched solution of Cu-65.

In this example the spiking of isotopes in uncomplexed forms is demonstrated to permit formation and equilibration rapidly enough to tag both elemental and speciated forms of the element of interest. In FIG. 5 the natural abundance of natural copper is shown. Natural copper has for example a ratio of Cu-63 and Cu-65 of 69.09% and 30.91% respectively. In FIG. 5 this ratio can be observed in a dilute electroplating solution. It will be appreciated that FIG. 5 showing Cu singly charged ions which exhibit the natural ratio, while FIG. 6 illustrates Cu ions after dynamic spiking with enriched Cu-65. In FIG. 6 an altered ratio is produced by the addition of a known quantity of 95% enriched separated Cu-65 isotope from a dilute nitric acid solution. The altered ratio created by the mixing of a diluted plating solution of natural isotopic composition and an isotopically enriched solution of Cu-65 (95% enrichment). This new ratio can now be used to determine the concentration of natural copper in the original solution. This data is made on a dilute solution of the previously described plating solution.

Figure 7:
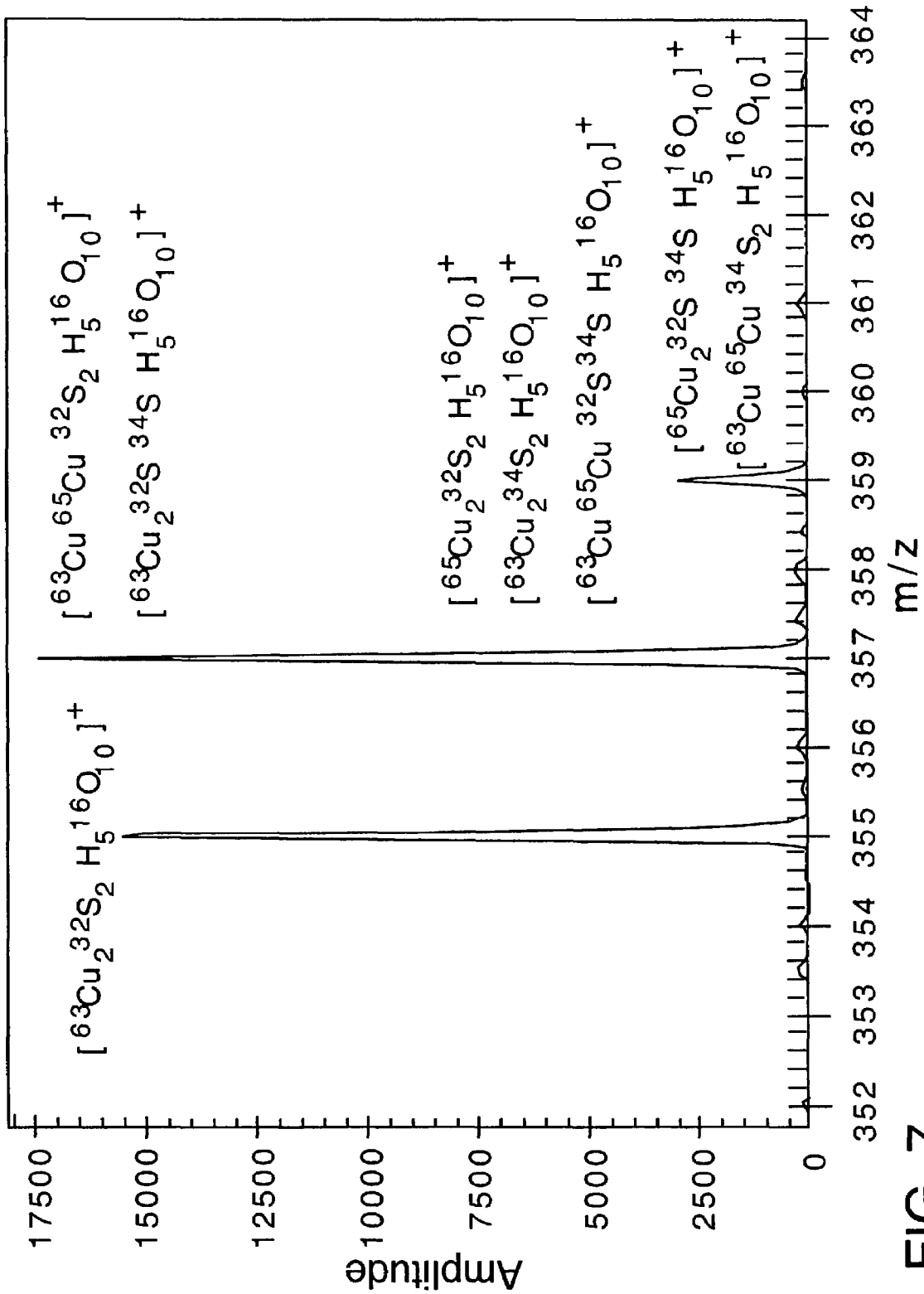
FIG. 7 illustrates the natural isotope pattern for a copper complex species measured in copper sulfate solution.

Using this ratio the concentration of copper can be determined without using any calibration curve and in a direct mixture in a flowing process stream by in-process isotope dilution mass spectrometry. At the same time from FIG. 4 the species centered near mass/charge 357 that is created from the plating solution and that may be one of the key plating structures that can be used for feedback control of the process is also spiked dynamically. FIG. 7 shows one of the complex species that is formed from the aqueous sulfate solution that is formed dynamically on-line in a flowing stream. This corresponds to the complex in FIG. 4 at near mass/charge 357. Each of these species is being tagged simultaneously in this dynamic tagging procedure. The quantitative measurement of each of the elemental and species is quantifiable in a similar way in a similar dynamic spiking procedure.

In FIG. 7 the individual natural isotopic species are displayed. Because this is a complex species there is a mathematically predictable pattern created by the dominant isotopes of the two heavy elements in this molecule, Cu and S respectively. The chemical formula of this species is Cu$_2$H$_5$O$_{10}$S$_2^\pm$. Because copper has two stable isotopes and sulfur has four isotopes with two dominant isotopes (S-32, 95.02%; S-33, 0.75%; S-34, 4.21% and S-36, 0.02%) a unique pattern is identifiable. FIG. 7 demonstrated the measured natural pattern observed for this copper sulfate species in this copper sulfuric acid solution.

Figure 8:
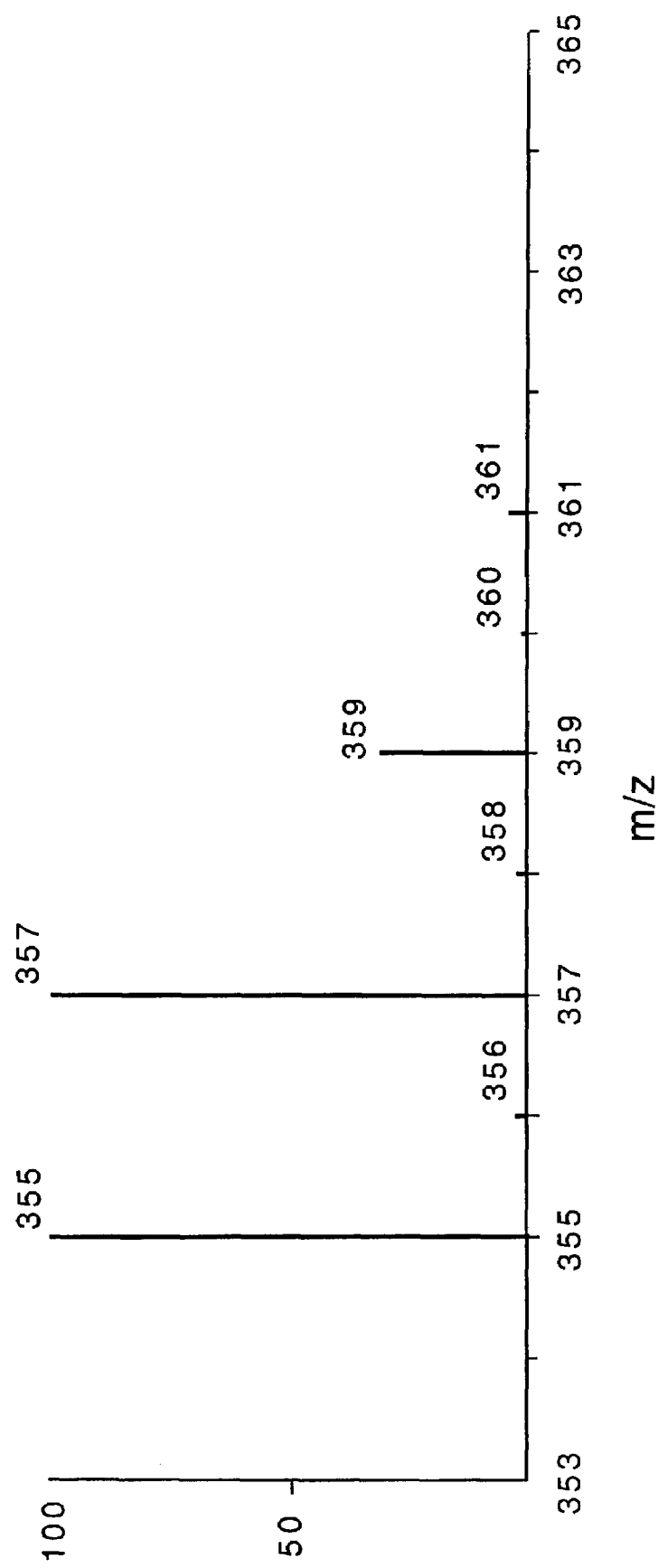
FIG. 8 illustrates a theoretical pattern for the dominant ions of the species having a solution of a copper species in a sulfate solution where the major isotopes of copper and sulfur are considered.

A theoretical pattern for the natural isotopic pattern of this species was calculated and is shown in FIG. 8. This pattern is essentially identical to the isotopic pattern shown in FIG. 7. For the isotope species of lowest mass, near m/z 355, there is a match between the theoretical and measured value 354.7916 and 354.7922 atomic mass units (a.m.u.) respectively.

The isotopic pattern identifies the specie but does not quantify it. Quantification of fragile multiple species simultaneously observed from a parent element has not been shown in the prior art. The quantification of this species using classical means of calibration could not be accomplished as there would be no way to produce this species in this solution exclusively and to make that classical measurement. The present invention produces a way of quantifying a unique fragile species that is too delicate to be synthesized and isolated and a way of making that quantification along with many other quantitative identifications simultaneously.

The method of dynamic species spiking has been described in a patent incorporated herein by reference. The present improvement is the simultaneous dynamic spiking of inorganic and multiple species and the quantitative identification of these species.

Figure 9:
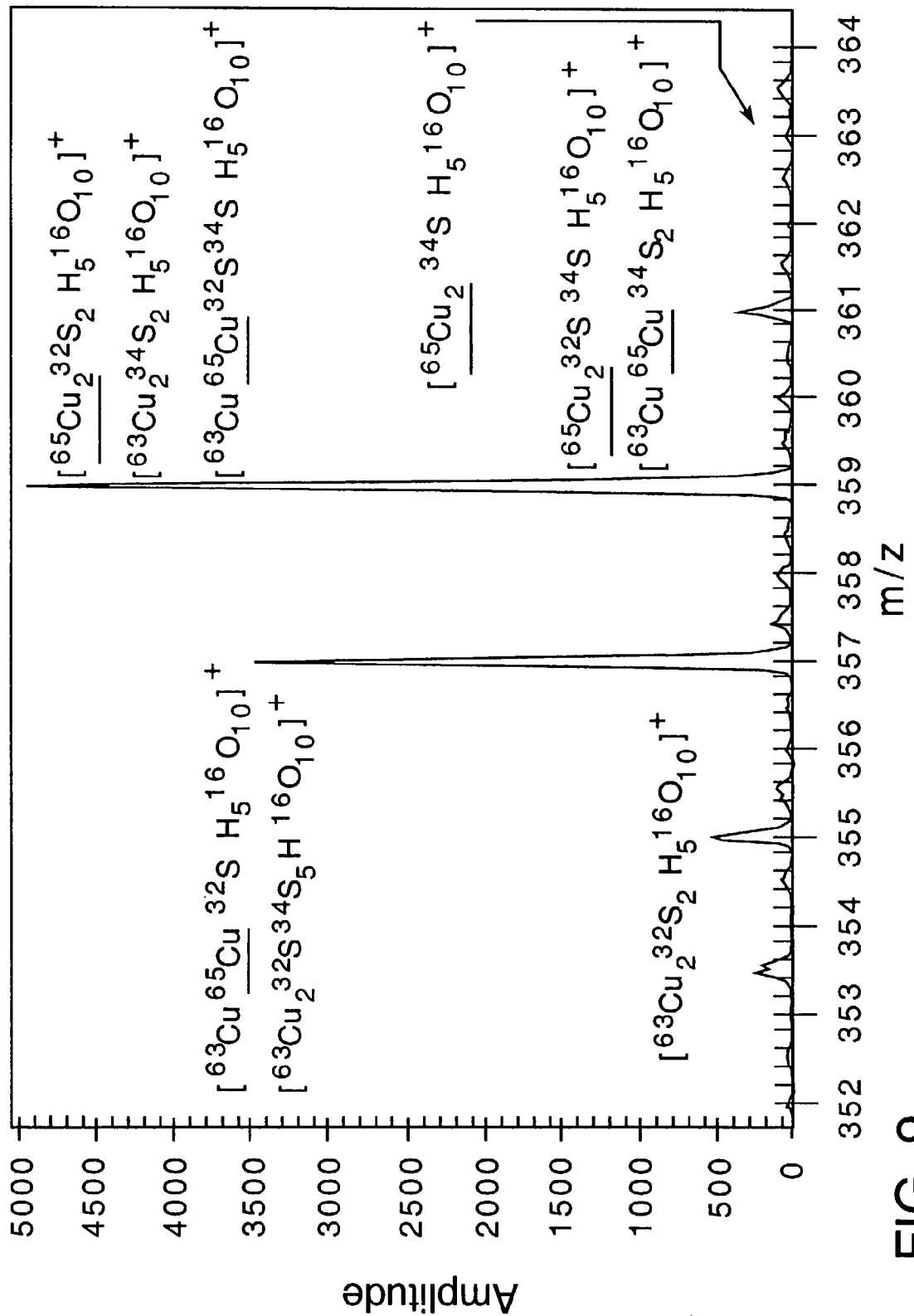
FIG. 9 illustrates isotopically enriched species showing the enriched isotope incorporated and shifting the species pattern from that of the normal pattern to species incorporating enriched copper-65 and are indicated where the enriched isotopes are incorporated.

FIG. 9. The isotopically enriched species is of the molecular form Cu$_2$H$_5$O$_{10}$S$_2^\pm$ where the enriched isotope incorporated and shifting this species patterns from that of the normal pattern shows the highlighted enriched incorporated Cu-65 responsible for the unique separated isotopically enriched species.

In this case, both the inorganic ion and multiple species have been dynamically spiked on-line and in-process in near real time. This represents a departure from previous methods where single species are isotopically spiked with known molecular forms of the target analyte. Here the spiking is dynamic and conforms to the complexity of the solution. All forms can be compared to the known isotopic concentration added and a known amount of that isotopic solution. Classical IDMS and SIDMS methods can be used on multiple species to determine the quantitative elemental and species simultaneously present in the solution. This method introduced two new aspects to quantitative identification. The dynamic spiking and the ability to quantify fragile species that could not be known using classical methods of calibration.

The second method involves spiking the sample solution with species that are already formed of specific compounds synthetically and when added to the solution produce the same SIDMS and IPMS capabilities previously described. They permit in-process or on-line speciated isotope dilution mass spectrometry (SIDMS) of the analyte species in the in-process solutions. Isotopically labeled species such as those of the accelerators and suppressors and ligands are determined using these isotopically enriched molecular and complex forms both qualitatively and quantitatively.

Isotopic in-process analysis also enables transport of samples over greater distances. This is accomplished by spiking the sample at the remote source, thus preventing solution component changes during transport from introducing error in the measurement of the process solutions analytes. When samples are spiked immediately at the source prior to transport they resist alterations in transport from biasing the results from losses and species transformations. Usually losses from tubing walls, such as adsorption or ion exchange and incomplete transport of the sample, would cause measurement bias and errors. These biases are avoided by spiking at the remote site prior to transportations. Once spiked with enriched isotopically labeled analytes of interest, the sample analysis using SIDMS and IPMS is not affected by losses that occur in transport. The ratio remains constant and is not biased by losses in transport. Additionally, any transformations of the species that may occur in transport are detected as labeled byproducts when analyzed and subordinate species are identifiable as tagged species. The species tags are done by either or both the dynamic process and/or by synthetic methods done separately and spiked into the in-process solutions.

Figure 10:
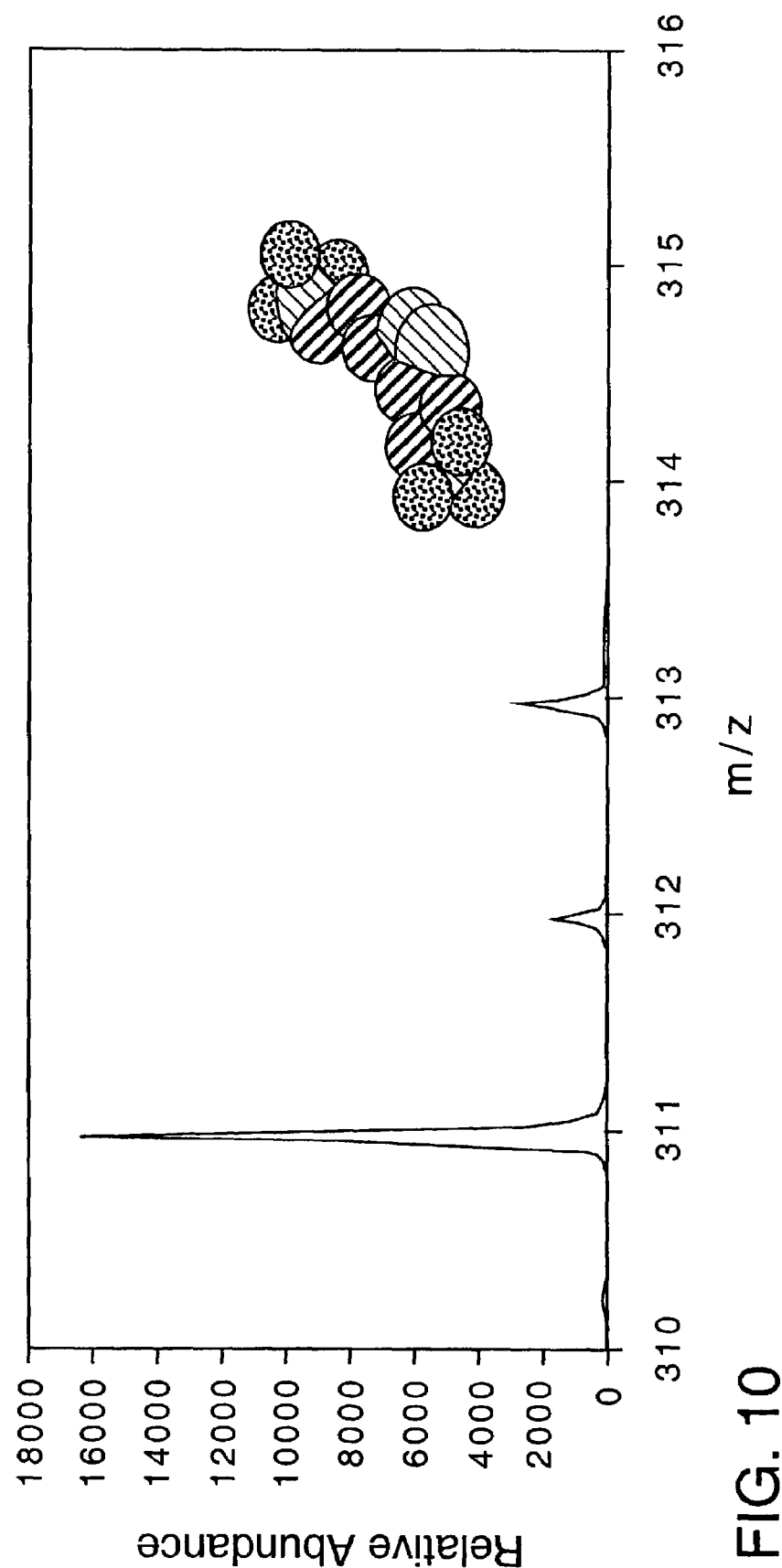
FIG. 10 illustrates a distinctive isotope pattern of a specific disulfide, bis(3-sulfopropyl)disulfide.

FIG. 10. shows distinctive isotope pattern of bis(3-sulfopropyl)disulfide that can be used to derive a consistent chemical formulation of $(C_6H_{15}S_4O_6)^+$. The ratios of the peaks in this pattern can be altered with synthetically produced enriched standard spikes, and the bis(3-sulfopropyl)disulfide quantified using IPMS.

Figure 11:
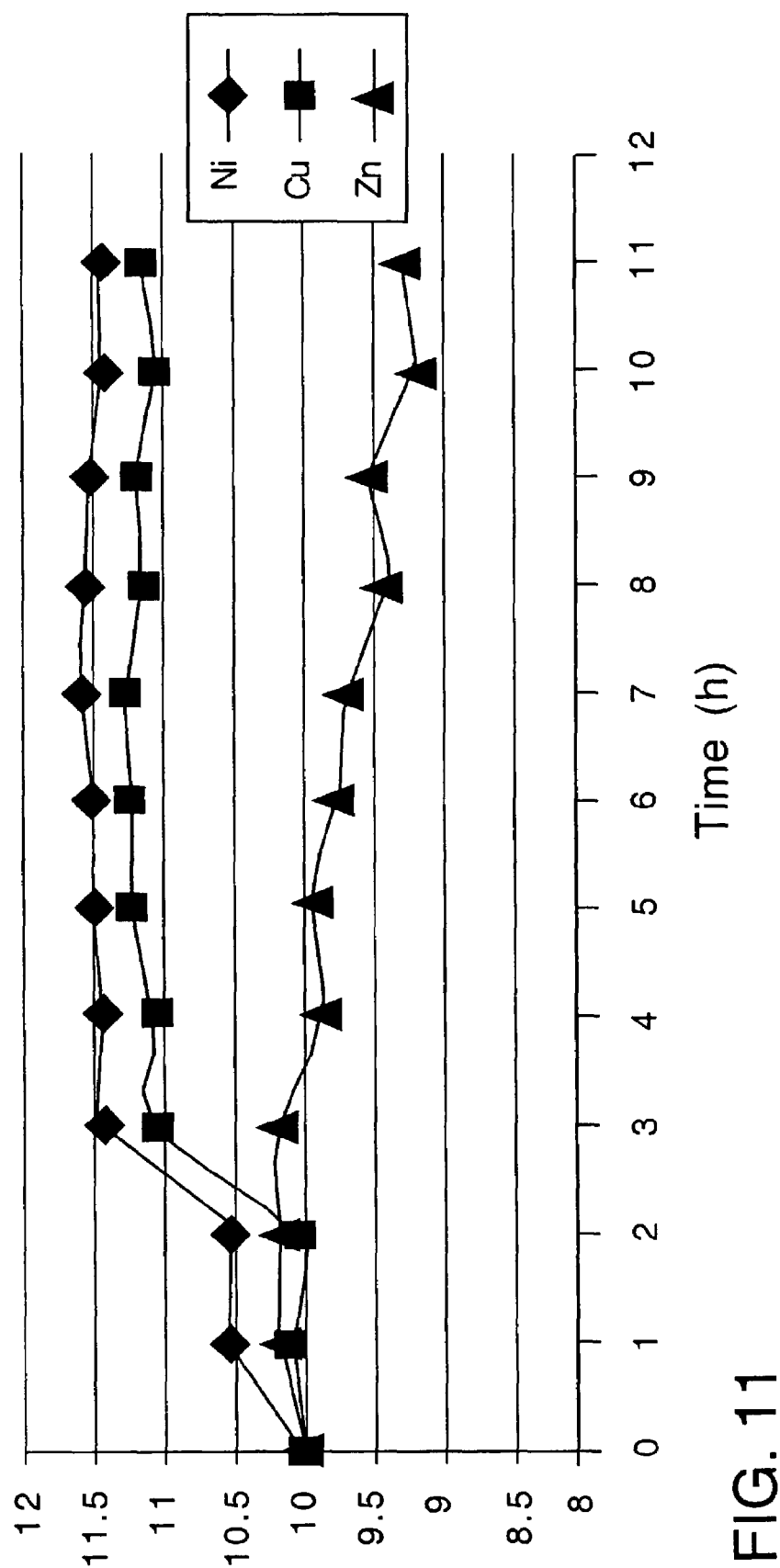
FIG. 11 illustrates a comparison of 12 hour operation of an electrospray mass spectrometer with traditional calibration curves for quantitation of nickel, copper and zinc.

Calibration using in-process addition of enriched isotopes as opposed to traditional calibration curves provides the ability to not require stability of the measurement system including all major components including the ionization source, sample handling hardware and the mass spectrometer. This is demonstrated here by using a long-term quantitative evaluation permitting ion source fluctuations, mass spectrometer fluctuations and instrument automation fluctuations. FIG. 11 shows a twelve-hour operation of electrospray mass spectrometer with traditional calibration curves for quantitation of Cu, Ni and Zn.

FIG. 11 demonstrates the normal mass spectrometric drift of a mass spectrometer with time. In this case the instrument was initially calibrated and then used for 12 hours without recalibration. In this example the Cu and Ni drift up by 15% and the Zn drifts down by 10% over this same time period due to the fluctuations normally encountered in a complex analytical tool.

Figure 12:
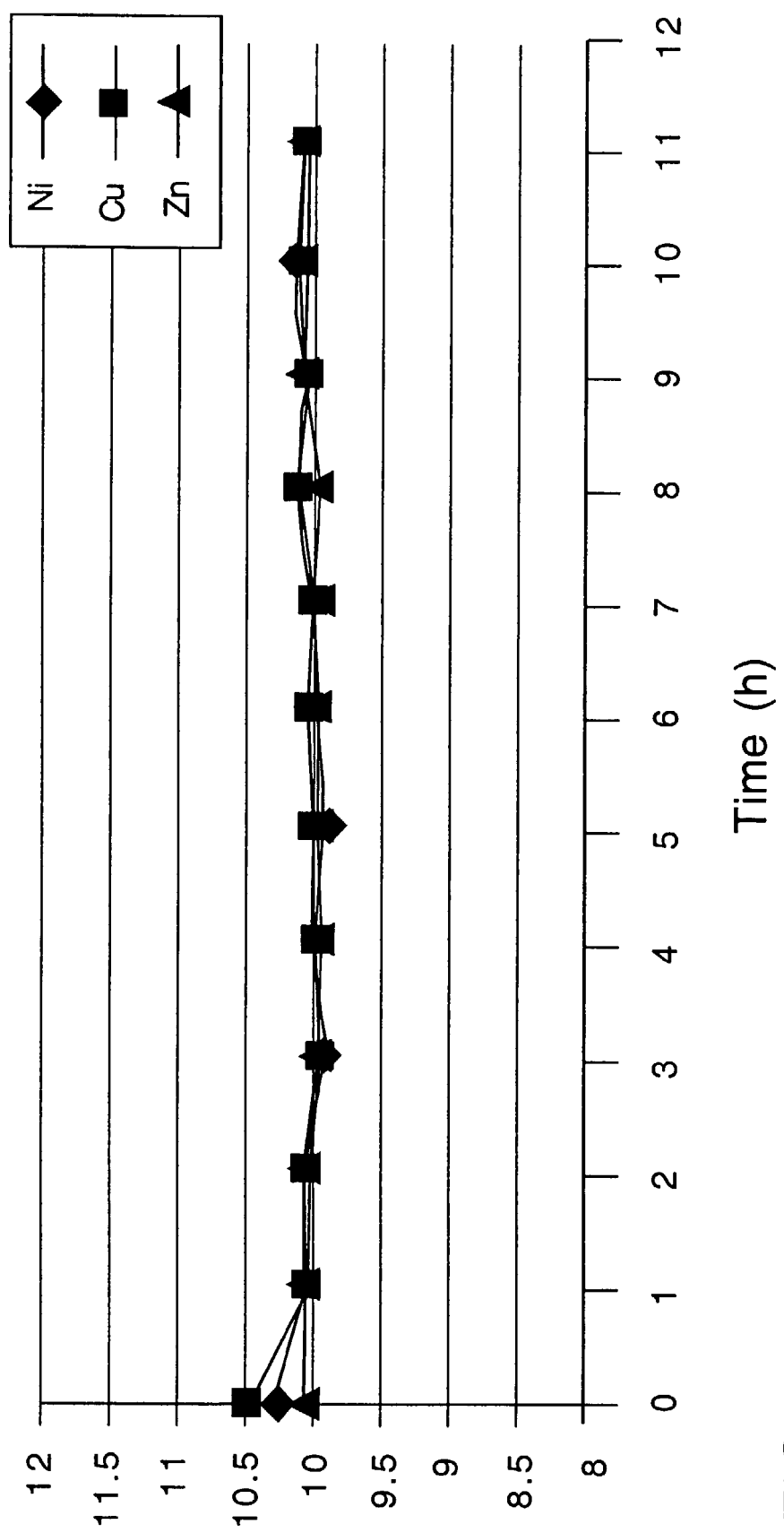
FIG. 12 shows a 12 hour operation of electrospray mass spectrometer using IPMS for quantitation of copper, nickel and zinc.

Using in-process addition of isotopic spikes enabling the isotopic ratio to be used as the calibration method over this same time period FIG. 12, which illustrates a twelve-hour operation of electrospray mass spectrometer using IPMS for quantitation of Cu, Ni and Zn, demonstrates the stability within measurement statistical limits and returns consistent virtually identical concentrations despite the drift of the instrument. This system permits the instrument to continue to drift and alter the absolute intensity while measuring the isotopic ratios to establish the concentration. This method eliminates the need to use of traditional separate calibration curve measurements. In addition there is no separate calibration procedure and each measurement becomes a direct measurement of concentration of element, species and/or molecule.

Figure 13:
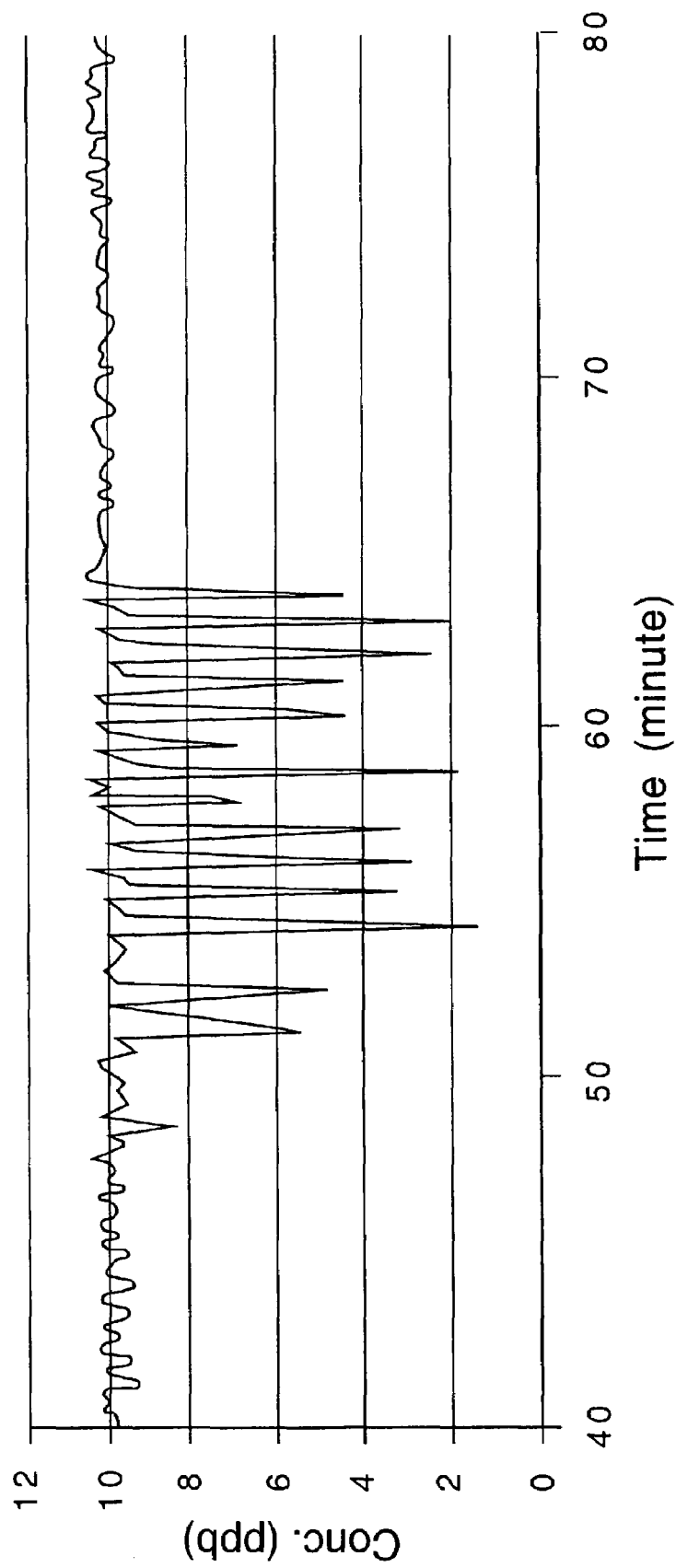
FIG. 13 illustrates copper signal instability most likely caused by air bubbles in the sample stream.

Another example of how the quantitation effects of intensity drift of the mass spectrometer are reduced or essentially eliminated by IPMS is included. Direct analysis using in-process isotope measurement permits the use of a less stable ion source such as the electrospray as the fluctuations in the source and also those of the instrument have little or no effect on the quantitation of the instrument. In addition, instrument manipulation of the sample, such as the switching of valves or the presence of trapped gas bubbles that would normally cause an absolute change in signal intensity, does not affect the accuracy of the instrument. This is demonstrated in FIG. 13. FIG. 13 shows copper signal instability most likely caused by air bubbles in the sample stream resulting in up to 80% decreases in signal and violent instrument signal instability. Actual sample introduction is a concentration of 10 ppb copper with the concentration determined by traditional calibration means.

In this figure copper is being measured during valve and solution manipulation. In this case a series of bubbles has entered the instrument and interrupted the sample introduction to the instrument causing large fluctuations and periodic reductions in the total ion intensity. These interruptions affect the ionization source and mass spectrometer and the general stability of the measurement. This would normally make it impossible to achieve quantitative measurements. The reduction in signal at several points exceeds 80% signal intensity reduction.

The fluctuations shown in FIG. 13 are minimized when using IPMS as a quantitative measurement of the 10 ppb copper in this example.

Figure 14:
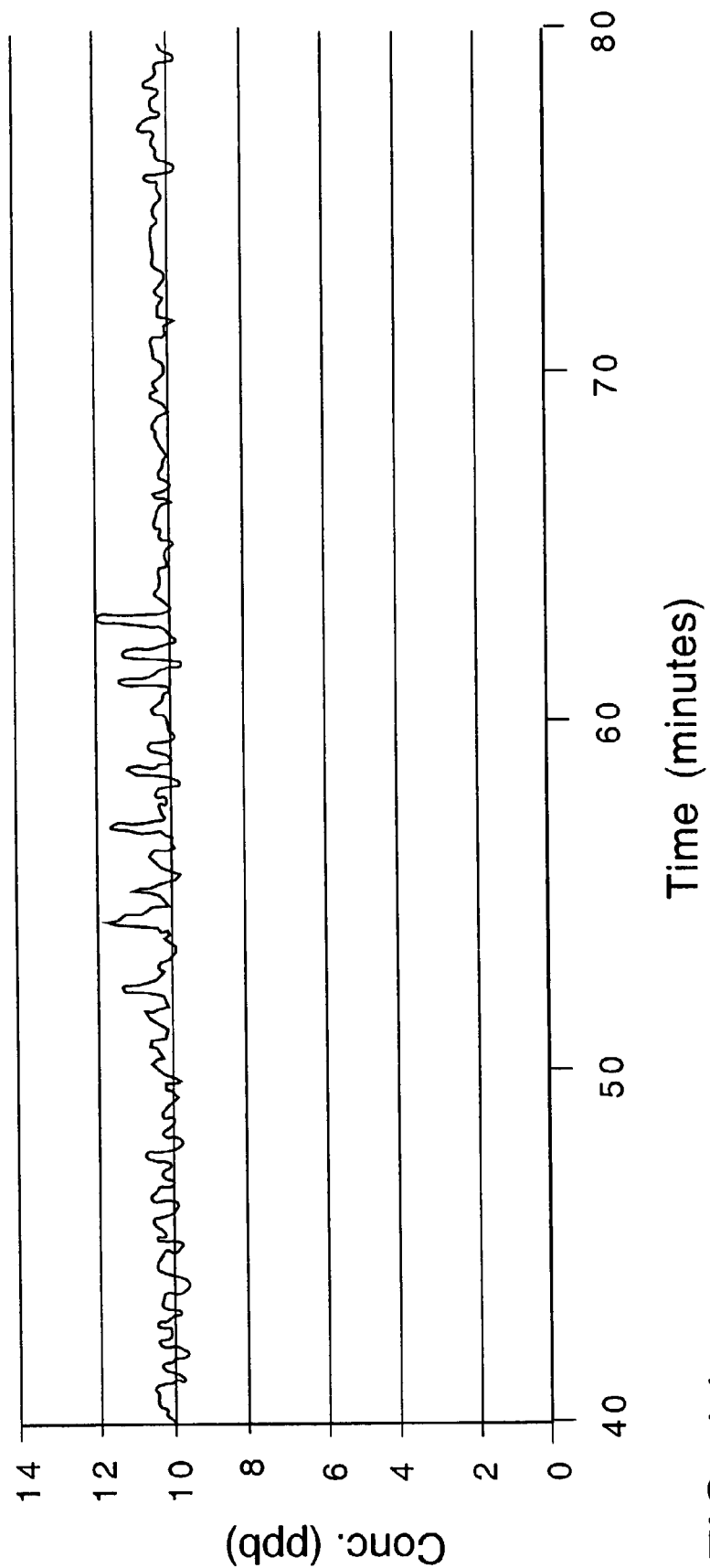
FIG. 14 illustrates copper signal instability most likely caused by air bubbles being reduced by using IPMS to quantify the measurement of copper.

FIG. 14 shows copper signal instability most likely caused by air bubbles is dramatically reduced using IPMS to quantify the measurement of 10 ppb copper. Here the ratio was calculated by peak height or peak area in the mass spectrometer and the deviations caused by the presence of bubbles are reduced to less than 20%. FIG. 14 demonstrates the same quantitative data for 10 ppb copper using isotopic ratios to quantify the measurement and essentially eliminate the effect of the instrumental and solution process noise.

This invention additionally differs from prior art in that no prior separation is required to make these measurements. In this method direct analysis of a plurality of analytes such as elements, species and organic constituents is made together and simultaneously without prior separation. This permits the correlation of all components affecting the chemical process in a single measurement.

Figure 15:
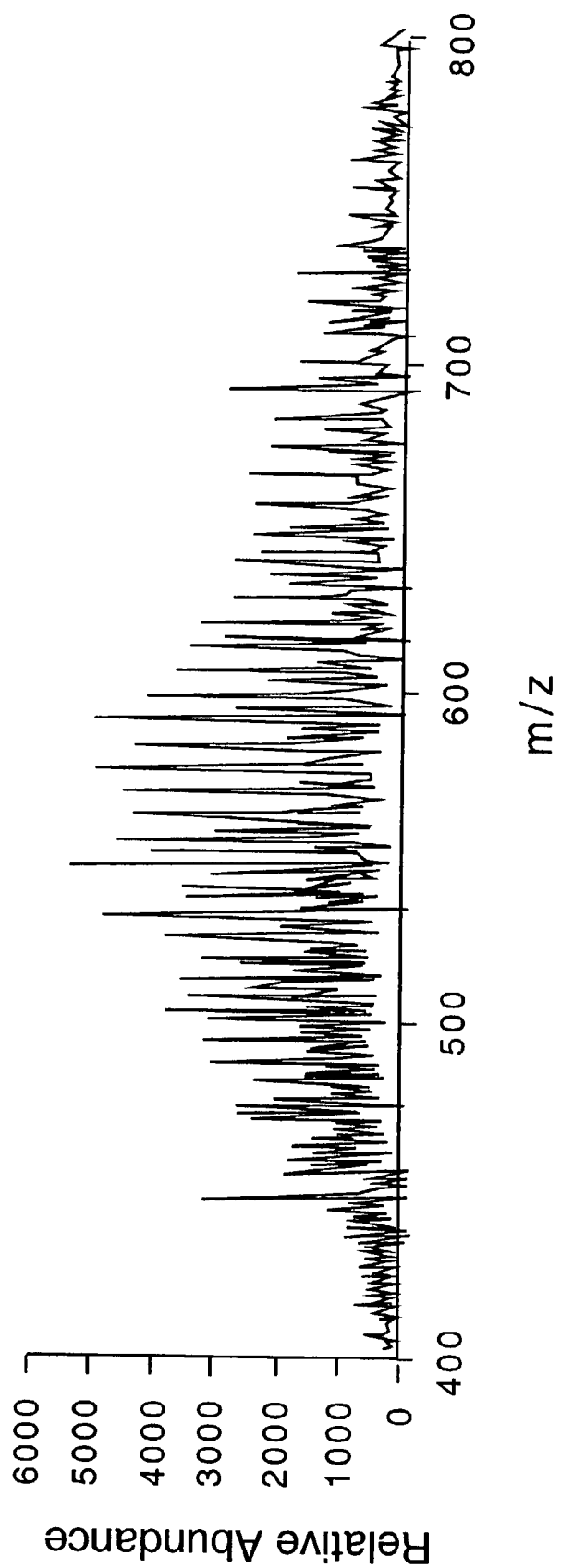
FIG. 15 illustrates a IP API-MS spectra of polyethylene glycol.

The time-of-flight section of the instrument provides the mass resolution needed to quantify and characterize dissolved polymers and monitor polymeric decomposition in said solutions. FIG. 15 shows a spectrum highlighting the molecular weight distribution of a polymer used as a "suppressor" in a copper plating solution. It shows an IP-API-MS spectra of polyethylene glycol suppressor of 3600 MW.

Figure 16:
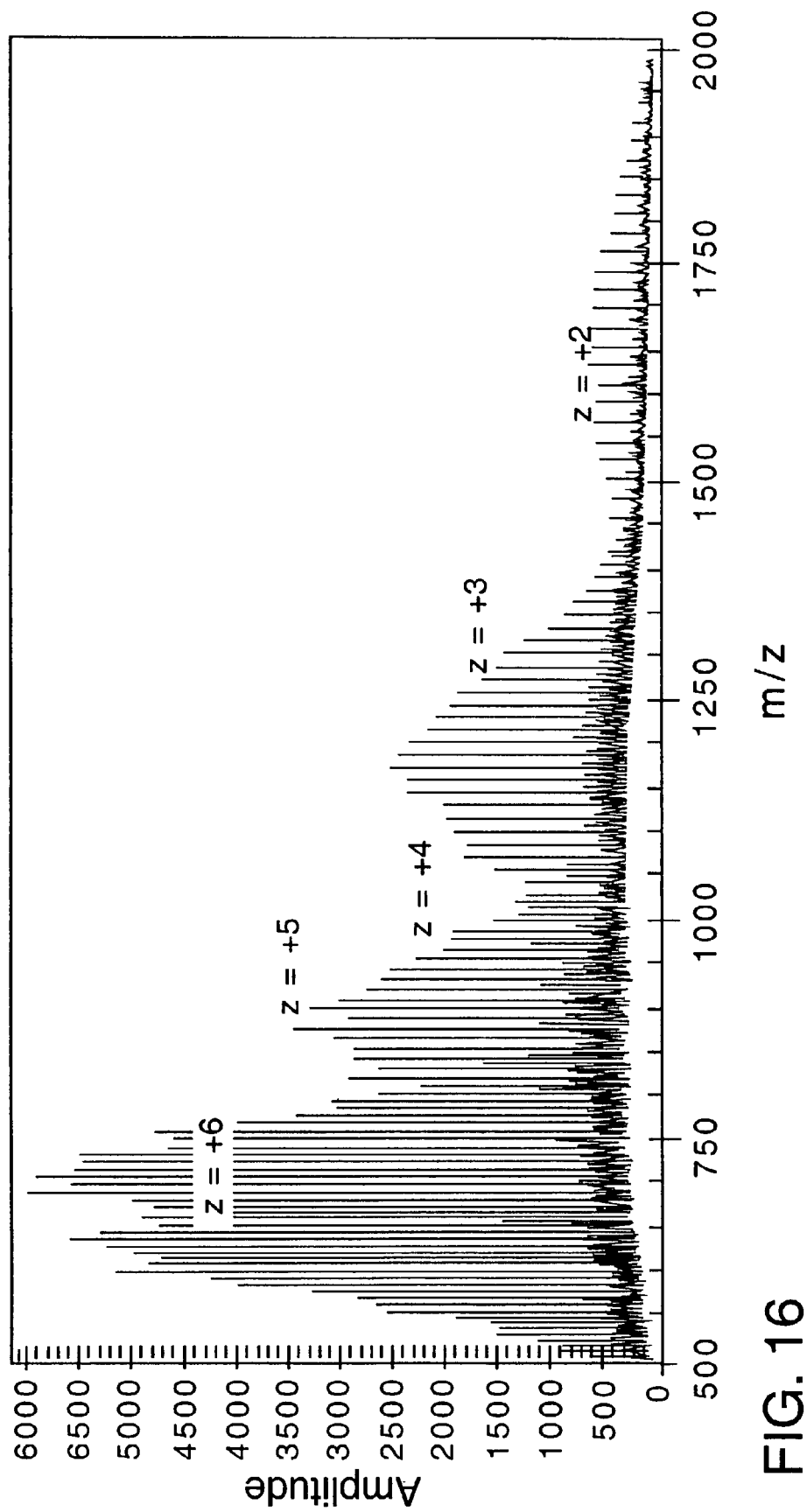
FIG. 16 illustrates a plot of amplitude versus mass to charge for multiple charges on polyethylene glycol formed by solution additions.

However, the mass-spectrum window m/z=475-700 (FIG. 15) does not show the pattern of peaks separated by 44.0 a.m.u. that one would expect from a polyethylene glycol polymer; but it does feature evenly spaced peaks. Further analysis of the FIG. 16 PEG solution with adducts of sodium showing the spectra can be clarified as a serial distribution of peaks divided by evenly spaced separations.

Figure 17:
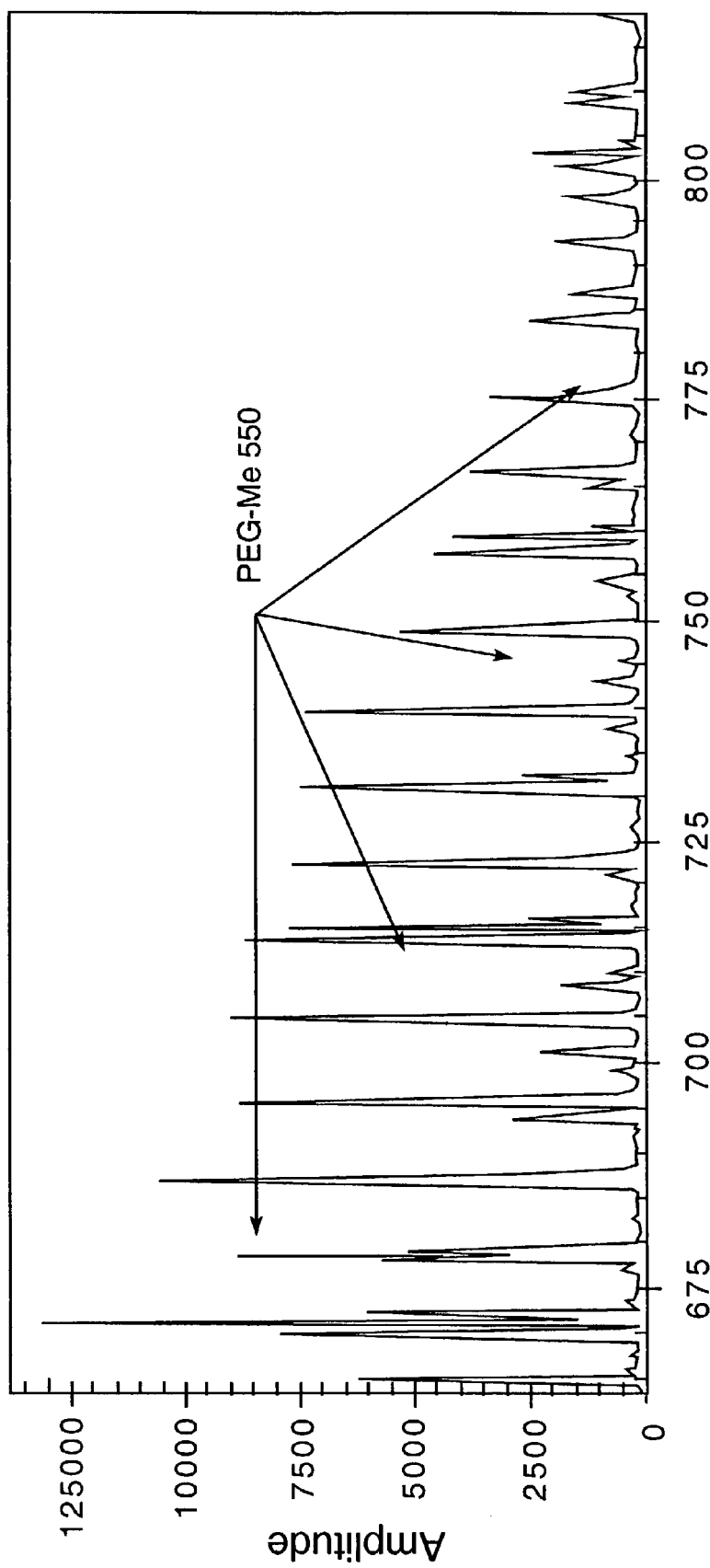
FIG. 17 is a mass spectrometer plot of amplitude versus mass to charge for a mixture of PEG 3600 and the internal standard PEG-Me-550 employing sodium ion as the cation adduct.

Use of a known concentration of a different molecular weight polymer with the same polymer backbone or a known concentration of one with a different terminal end group will result in a series of peaks slightly shifted from those of the polymer under consideration. Since the concentration of the internal standard polymer is known and a relationship between the two polymers has been experimentally established previously, then the concentration of the unknown polymer can be determined. Using this technique can both quantify the polymer of interest and identify when the polymer begins to decompose as peak heights will decrease with respect to the internal standard polymer. This technique is illustrated in the following FIG. 17 where a mass spectrum of PEG with an average molecular weight of 3600 is mixed with an internal standard of PEG with an average molecular weight of 550 and a methoxide Me terminal group. Here the z=+5 group is expanded to show the nearby peaks from the internal standard PEG-Me-550.

EXAMPLE

An example of an acid copper plating solution will be considered.

| Constituent | Range of Amounts in ppm |
|---|---|
| $Cu^{2+}$ (from $CuSO_4$) | 10-20,000 |
| $Cl^-$ (from HCl) | 40-160 |
| Organic additives (one or more) | |
| Leveler (such as a polyalkyleneimine) | 1-50 |
| Accelerator (such as a sulfo sulfonate) | 10-50 |
| Suppressor (such as a polyether additive) | 10-1000 |

In addition, the solution might contain impurities.

The present invention facilitates maintaining the plating solution within the desired chemical ranges.

While for convenience of disclosure emphasis has been placed on use in an in-process solution which was employed in an electroplating process, it will be appreciated that the invention is not so limited and may be employed advantageously in many other solution analyses. For example, it might be employed in connection with nuclear process cooling water, drinking water or monitoring water for environmental purposes.

In nuclear process cooling water, the maintenance, and sometimes reduction, of metals and complex ions to low levels such as 10 ng/g and frequently as low as 10 pg/g is essential in nuclear cooling water. The exposure to neutron flux causes adsorption of neutrons and conversion to radioactive elements. Some species also cause corrosion and malfunction of some critical components of the cooling systems and the concentrations in the cooling systems is critical to reliable use and flushing and environmental disposal of the cooling water. The monitoring of these parameters on-line and in near real time is critical to correction and optimization of these systems and to prevent expensive remediation of the cooling systems and discharge sites.

Drinking water and objects containing potable water, are another example of another critical area where real-time monitoring is essential to meet identified national priority needs. For such samples dilution would not generally be required. One of the scenarios that have recently been identified is not only the monitoring for common health contaminants, but also fast response monitoring for toxins intentionally placed in water. The distribution systems of water systems worldwide are generally unprotected from chemical intervention directly into the distribution systems. Any building or complex or hotel or resort or government building is a potential target. Monitoring at present is done in the distribution as few as one to six times yearly and results downstream from the distribution centers are only monitored for leaks of sewage an other natural occurrences and are not monitored in any real time for toxic materials and are not equipped for deliberate contamination. Every faucet is a potential entry point being backpressure induced by a terrorist or mentally imbalanced individual or group of individuals. Real-time measurements of over 300 common compounds simultaneously including inorganics, organics, organometalics, complex species, and bacterial and viral agents could be provided in a real-time instrument based system. Simple sophisticated measurements of not only elements but species are necessary as the toxicity of specific species may be six orders of magnitude more toxic than a metal ion that would be analyzed by less sophisticated instruments. Many species of this type are in the environmental and medical literature. An instrument that has the detection capability of masses 2 to 45,000 a.m.u with resolution that permits it to detect all of these materials simultaneously and with accuracy and speed would be desirable. Transport to the instrument from multiple sites without compromise in analytical detection could provide for effectiveness as are many of other unique instrument system automated attributes. This protection monitoring system is only feasible as an automated system. It must function 24 hours a day and for extended periods of time and produce a regiment of disciplined examination repetitively and validate its findings using advanced analytical algorithmic methods which may be unique in a variety of water systems. All of these attributes also apply to the inclusion of water in other consumables as the source and the final product has similar attributes.

Similarly, environmental evaluations of liquids to monitor for contamination, remediation and compliance with legal requirements may be provided with the present invention.

It will be appreciated that the present invention has provided an effective method and related apparatus for in-process, automated analysis and characterization of a plurality of analytes of process solutions.

It will be appreciated, therefore, that the present invention provides an effective, automated method and apparatus for analysis of chemical analytes in a process solution. It advantageously may be employed in-process. The present invention not only facilitates analysis of a process solution at or adjacent to the vessel from which the sample for analysis was taken, but also facilitates delivery of the solution sample to a remote location for analysis, preferably after pretreatment which resists undesired changes of the sample in transit.

Whereas particular embodiments have been described herein for purposes of illustration, it will be evident to those skilled in the art that numerous variations of the details may be made without departing from the invention as defined in the appended claims.

We claim:

1. An apparatus for automated analysis of a constituent of a process solution, comprising:
- a sample extraction module operable to extract a sample of known volume from the process solution;
- a first spike container for containing isotopically-labeled spike;
- a second spike container for containing an internal standard;
- a sample dilution module operable to dilute the sample to provide a diluted sample;
- a mixer for mixing the diluted sample and a spike selected from the first spike container or the second spike container to allow equilibration to occur therebetween;
- an atmospheric pressure ionizer operable to ionize the equilibrated diluted sample and spike mixture to produce ions;
- a mass spectrometer operable to process the ions to provide a ratio response; and
- a control system operable to control a cyclic extraction of samples, dilution of the samples, spiking of the diluted samples, ionization of the spiked diluted samples, processing of the ions to provide ratio responses, and processing of the ratio responses to characterize the concentration of the constituent in the process solution over time.

2. The apparatus of claim 1, wherein the sample dilution module is configured to chemically modify the diluted samples.

3. The apparatus of claim 1, wherein the control system is configured to control the dilution of the samples such that the dilution is sufficient to optimize the characterization of the concentration of the constituent.

4. The apparatus of claim 1, wherein the atmospheric pressure ionizer is an electrospray ionizer.

5. The apparatus of claim 1, wherein the mass spectrometer is remotely located from the process solution.

* * * * *